United States Patent
Murata et al.

(10) Patent No.: US 9,840,527 B2
(45) Date of Patent: Dec. 12, 2017

(54) METAL COMPLEX INCLUDING TRIDENTATE AMINODICARBENE LIGAND AND HYDROGENATION REDUCTION METHOD USING SAME

(71) Applicant: KURARAY CO., LTD., Kurashiki-shi (JP)

(72) Inventors: Yusuke Murata, Kurashiki (JP); Masahiro Torihara, Kurashiki (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 14/899,424

(22) PCT Filed: Jun. 19, 2014

(86) PCT No.: PCT/JP2014/066268
§ 371 (c)(1),
(2) Date: Dec. 17, 2015

(87) PCT Pub. No.: WO2014/203963
PCT Pub. Date: Dec. 24, 2014

(65) Prior Publication Data
US 2016/0145282 A1   May 26, 2016

(30) Foreign Application Priority Data

Jun. 20, 2013 (JP) ................. 2013-129677

(51) Int. Cl.
| | | |
|---|---|---|
| *C07F 15/00* | (2006.01) | |
| *B01J 31/24* | (2006.01) | |
| *C07C 29/145* | (2006.01) | |
| *C07C 29/149* | (2006.01) | |
| *C07C 31/125* | (2006.01) | |
| *C07C 31/20* | (2006.01) | |
| *C07C 33/22* | (2006.01) | |
| *C07F 1/10* | (2006.01) | |
| *C07B 31/00* | (2006.01) | |

(52) U.S. Cl.
CPC .......... *C07F 15/0046* (2013.01); *B01J 31/24* (2013.01); *B01J 31/2404* (2013.01); *C07B 31/00* (2013.01); *C07C 29/145* (2013.01); *C07C 29/149* (2013.01); *C07C 31/125* (2013.01); *C07C 31/20* (2013.01); *C07C 33/22* (2013.01); *C07F 1/10* (2013.01); *B01J 2231/643* (2013.01); *B01J 2531/821* (2013.01)

(58) Field of Classification Search
CPC ............................... C07F 15/0046
See application file for complete search history.

(56) References Cited

U.S. PATENT DOCUMENTS

| | | |
|---|---|---|
| 2011/0070152 A1 | 3/2011 | Abdur-Rashid et al. |
| 2011/0237814 A1 | 9/2011 | Kuriyama et al. |
| 2012/0010417 A1 | 1/2012 | Hagiya et al. |
| 2012/0253042 A1 | 10/2012 | Milstein et al. |

FOREIGN PATENT DOCUMENTS

| | | |
|---|---|---|
| JP | 2008 537946 | 10/2008 |
| JP | 2008 538352 | 10/2008 |
| JP | 2010 527316 | 8/2010 |
| WO | 2010 114137 | 10/2010 |
| WO | 2011 048727 | 4/2011 |
| WO | 2012 052996 | 4/2012 |
| WO | 2013 023307 | 2/2013 |
| WO | 2013 024119 | 2/2013 |

OTHER PUBLICATIONS

Danopoulos et al. "Stable N-functionalised 'pincer' bis carbene ligands and their ruthenium complexes; synthesis and catalytic studies" Chemical Communications, 2002, pp. 1376-1377.*
Poyatos et al., "New Ruthenium(II) CNC-Pincer Bis(carbene) Complexes: Synthesis and Catalytic Activity," Organometallics, vol. 22, (2003), pp. 1110-1114.
Hernandez-Juarez et al., "Hydrogenation of imines catalyzed by ruthenium(II) complexes based on lutidine-derived CNC pincer ligandst," Dalton Transactions, vol. 42, (2013), pp. 351-354.
Sun et al., "Ester hydrogenation catalyzed by Ru-CNN pincer complexes," Chemical Communications, vol. 47, (2011), pp. 8349-8351.
International Search Report Issued Sep. 2, 2014 in PCT/JP14/066268 Filed Jun. 19, 2014.

* cited by examiner

*Primary Examiner* — Joseph R Kosack
(74) *Attorney, Agent, or Firm* — Oblon, McClelland, Maier & Neustadt, L.L.P.

(57) ABSTRACT

The use of a metal complex containing a ruthenium ion or an osmium ion, and a tridentate aminodicarbene ligand, the tridentate aminodicarbene ligand having one secondary amino group and two specific heterocyclic carbene groups sandwiching the amino group, enables hydrogenation reduction of carbonyl compounds, such as ketones, carboxylic acid esters, lactones, carboxylic acid amides, and lactams, and imine compounds under relatively mild conditions to produce corresponding alcohols, amines, and the like in a high yield with high catalytic efficiency. The metal complex is obtained by a method comprising steps of reacting a specific metal compound with a specific aminodicarbene precursor and subsequently reacting a specific compound. Reduction of a carbonyl compound or an imine compound in the presence of this metal complex using a hydrogen donor makes it possible to reduce the carbonyl compound or imine compound by hydrogenation.

14 Claims, 1 Drawing Sheet

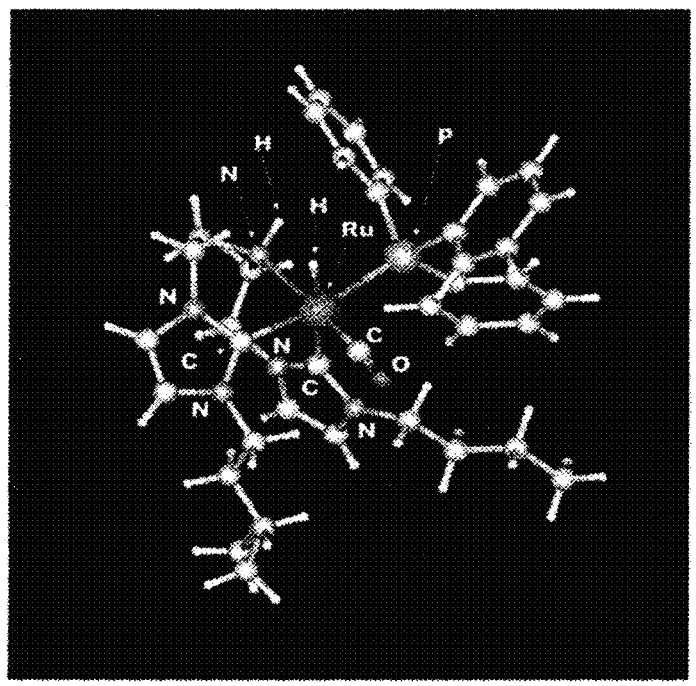

METAL COMPLEX INCLUDING TRIDENTATE AMINODICARBENE LIGAND AND HYDROGENATION REDUCTION METHOD USING SAME

TECHNICAL FIELD

The present invention relates to a metal complex containing a specific tridentate aminodicarbene ligand and a specific ion; a method for producing alcohols, diols, amines, amino alcohols, or the like by reducing carbonyl compounds or imine compounds by hydrogenation using the complex; or a hydrogenation reduction method using the complex.

BACKGROUND ART

Methods for reduction of carbonyl compounds, such as ketones, carboxylic acid esters, lactones, carboxylic acid amides, and lactams, and imine compounds to obtain corresponding alcohols, amines, and the like are important in chemical synthesis. Considering the decrease in by-products, easy operation, labor safety, and the like, a catalytic reduction method, which uses a catalyst, in particular, is useful for producing alcohols, amines, and the like. As one of such reduction catalysts, for example, ruthenium complexes having a multidentate ligand are known.

Many methods have been proposed, such as a method for reduction of carboxylic acid esters by hydrogenation using, for example, a ruthenium complex having bidentate or quadridentate aminophosphine as a ligand (Patent Literature (PTL) 1 and 2), a ruthenium complex having tridentate aminodiphosphine as a ligand (PTL 3), or a ruthenium complex having pyridine ring as a ligand (PTL 4 and Non-patent Literature (NPL) 1).

Further, PTL 5 discloses a method for reduction of carboxylic acid esters by hydrogenation using a ruthenium complex that is obtained by reacting imidazolium salt having at least one optionally substituted amino group with a ruthenium compound in the presence of a base. PTL 5 discloses a ruthenium complex having an aminocarbene ligand, which is a bidentate ligand obtained by reacting an imidazolium salt with a base.

CITATION LIST

Patent Literature

PTL 1: JP2008-538352A
PTL 2: JP2008-537946A
PTL 3: WO 2011/048727
PTL 4: WO 2012/052996
PTL 5: WO 2010/114137

Non-Patent Literature

NPL 1: Song, D. et al., Chemical Communications, 2011, 47, 8349-8351

SUMMARY OF INVENTION

Technical Problem

However, all of the hydrogenation reactions of carboxylic acid ester disclosed in PTL 1 to 5 and NPL 1 fail to achieve both satisfactory yield and catalytic efficiency, and are thus not considered to be economically advantageous. Further, all of the hydrogenation reduction methods disclosed in PTL 1 to 3 and 5 require a hydrogen pressure of 10 atmospheres or more, which poses problems in economic efficiency and operability to perform industrial production.

Therefore, an object of the present invention is to provide a metal complex capable of reducing by hydrogenation carbonyl compounds, such as ketones, carboxylic acid esters, lactones, carboxylic acid amide, and lactams, and imine compounds under relatively mild conditions to produce corresponding alcohols, amines, and the like in a high yield with high catalytic efficiency.

Solution to Problem

The present inventors conducted intensive research to achieve the above object. As a result, the present inventors succeeded in synthesizing a metal complex containing a ruthenium ion or an osmium ion, and a tridentate aminodicarbene ligand having one secondary amino group and two specific heterocyclic carbene groups sandwiching the amino group.

The present inventors further found that the metal complex synthesized in the present invention has high catalytic activity in the hydrogenation reduction of imine compounds and carbonyl compounds, such as ketones, carboxylic acid esters, lactones, carboxylic acid amides, and lactams.

The present inventors also found that the metal complex synthesized in the present invention surprisingly achieves a much higher yield and catalytic efficiency than the metal complex disclosed in PTL 5, which comprises a bidentate aminocarbene ligand and ruthenium. The metal complex disclosed in, in particular, PTL 5 has a higher yield and catalytic efficiency, compared with hitherto known metal complexes.

The present inventors then conducted further research.

The present invention has thus been accomplished. More specifically, the present invention encompasses the following (1) to (16).

(1) A metal complex containing a ruthenium ion or an osmium ion, and a tridentate aminodicarbene ligand, the tridentate aminodicarbene ligand having one secondary amino group and two heterocyclic carbene groups sandwiching the amino group, the heterocyclic carbene groups being represented by Formula $L^1$ and/or Formula $L^2$:

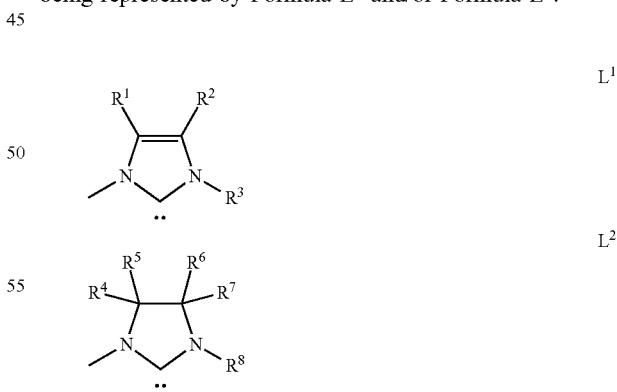

wherein $R^1$ to $R^3$ are identical or different and each independently represents hydrogen, halogen, hydroxy, oxyanion (—O⁻), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^1$ and $R^2$, and/or $R^2$ and $R^3$, taken together, form optionally substituted divalent hydrocarbon or optionally substituted divalent heteroatom-containing hydrocarbon; and $R^4$ to $R^8$ are identical or different and each independently represents hydrogen, halogen, hydroxy, oxyanion (—O$^-$), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^5$ and $R^6$, and/or $R^7$ and $R^8$, taken together, form optionally substituted divalent hydrocarbon or optionally substituted divalent heteroatom-containing hydrocarbon.

(2) The metal complex according to Item (1), wherein $R^1$ to $R^3$ are identical or different and each independently represents hydrogen, halogen, optionally substituted alkyl, optionally substituted cycloalkyl, optionally substituted aryl, optionally substituted heterocyclic, optionally substituted alkoxy, or optionally substituted aryloxy, or $R^1$ and $R^2$, and/or $R^2$ and $R^3$, taken together, form optionally substituted alkylene, optionally substituted alkenylene, or optionally substituted oxyalkylene; and $R^4$ to $R^8$ are identical or different and each independently represents hydrogen, halogen, optionally substituted alkyl, optionally substituted cycloalkyl, optionally substituted aryl, optionally substituted heterocyclic, optionally substituted alkoxy, or optionally substituted aryloxy, or $R^5$ and $R^6$, and/or $R^7$ and $R^8$, taken together, form optionally substituted alkylene, optionally substituted alkenylene, or optionally substituted oxyalkylene.

(3) The metal complex according to Item (1) or (2), wherein the tridentate aminodicarbene ligand is represented by Formula (1):

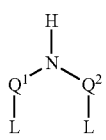

(1)

wherein $Q^1$ and $Q^2$ are identical or different and each represents optionally substituted $C_{1-5}$ alkylene or optionally substituted $C_{3-15}$ cycloalkylene, and two Ls are identical or different and each represents $L^1$ or $L^2$.

(4) The metal complex according to Item (3), wherein $Q^1$ and $Q^2$ are identical and each represents methylene, ethylene, or propylene.

(5) The metal complex according to any one of Items (1) to (4), wherein $R^3$ of Formula $L^1$ is optionally substituted alkyl, and $R^9$ of Formula $L^2$ is optionally substituted alkyl.

(6) The metal complex according to any one of Items (1) to (5), wherein $R^3$ of Formula $L^1$ is optionally substituted straight-chain alkyl, and $R^8$ of Formula $L^2$ is optionally substituted straight-chain alkyl.

(7) The metal complex according to any one of Items (1) to (6), wherein the metal complex has a composition represented by Formula (2) or (3):

[M(A)Y$^1$Y$^2$Z$^1$]  (2)

[M(A)Y$^1$Z$^1$Z$^2$]Y$^2$  (3)

wherein

M is a ruthenium ion or an osmium ion,

A is a tridentate aminodicarbene ligand, $Y^1$ and $Y^2$ are identical or different and each represents a monovalent anionic ligand, and $Z^1$ and $Z^2$ are identical or different and each represents a monodentate ligand.

(8) The metal complex according to Item (7), wherein the monodentate ligand represents CO; PR$^{1a}$R$^{1b}$R$^{1c}$, wherein $R^{1a}$, $R^{1b}$, and $R^{1c}$ are identical or different and each represents optionally substituted alkyl, optionally substituted cycloalkyl, optionally substituted aryl, or optionally substituted heterocyclic; P(OR$^{2a}$)(OR$^{2b}$)(OR$^{2c}$), wherein $R^{2a}$, $R^{2b}$, and $R^{2c}$ are identical or different and each represents optionally substituted alkyl, optionally substituted cycloalkyl, optionally substituted aryl, or optionally substituted heterocyclic; SR$^{3a}$R$^{3b}$, wherein $R^{3a}$ and $R^{3b}$ are identical or different and each represents optionally substituted alkyl, optionally substituted cycloalkyl, optionally substituted aryl, or optionally substituted heterocyclic; a nitrile compound; an isonitrile compound; $N_2$; $PF_3$; CS; tetrahydrothiophene; or $C_{1-5}$ alkene.

(9) The metal complex according to Item (7) or (8), wherein at least one of $Y^1$ and $Y^2$ of Formulae (2) and (3) is a halogen ion.

(10) The metal complex according to any one of Items (1) to (9), for use as a reduction catalyst for a reaction of reducing a carbonyl compound or an imine compound using a hydrogen donor.

(11) A method for producing a metal complex, the method comprising steps of reacting a metal compound (II) with an aminodicarbene precursor (I), and subsequently reacting the resulting product with a compound (III), wherein the aminodicarbene precursor (I) has one secondary amino group and two heterocyclic groups sandwiching the amino group, the two heterocyclic groups being represented by Formula $L^{1'}$ or $L^{2'}$:

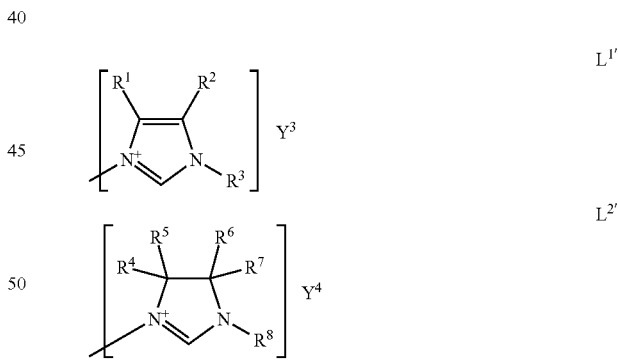

wherein $R^1$ to $R^3$ are identical or different and each independently represents hydrogen, halogen, hydroxyl, oxyanion (—O$^-$), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^1$ and $R^2$, and/or $R^2$ and $R^3$, taken together, form optionally substituted divalent hydrocarbon or optionally substituted divalent heteroatom-containing hydrocarbon;

$R^4$ to $R^8$ are identical or different and each independently represents hydrogen, halogen, hydroxyl, oxyanion (—O⁻), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^5$ and $R^6$, and/or $R^7$ and $R^9$, taken together, form optionally substituted divalent hydrocarbon or optionally substituted divalent heteroatom-containing hydrocarbon;

$Y^3$ represents an anionic ligand; and $Y^4$ represents an anionic ligand; and wherein the metal compound (II) contains a cobalt ion, a nickel ion, a copper ion, a rhodium ion, a palladium ion, or a silver ion, and wherein the compound (III) is represented by Formula (4):

$$MY^1Y^2Z_n \quad (4)$$

wherein M represents a ruthenium ion or an osmium ion, $Y^1$ and $Y^2$ are identical or different and each represents a monovalent anionic ligand, Z is identical or different and each represents a monodentate ligand, and n is an integer of 2 to 4.

(12) The method for producing a metal complex according to Item (11), wherein the monodentate ligand represents CO; $PR^{1a}R^{1b}R^{1c}$, wherein $R^{1a}$, $R^{1b}$, and $R^{1c}$ are identical or different and each represents optionally substituted alkyl, optionally substituted cycloalkyl, optionally substituted aryl, or optionally substituted heterocyclic; $P(OR^{2a})(OR^{2b})(OR^{2c})$, wherein $R^{2a}$, $R^{2b}$, and $R^{2c}$ are identical or different and each represents optionally substituted alkyl, optionally substituted cycloalkyl, optionally substituted aryl, or optionally substituted heterocyclic; $SR^{3a}R^{3b}$, wherein $R^{3a}$ and $R^{3b}$ are identical or different and each represents optionally substituted alkyl, optionally substituted cycloalkyl, optionally substituted aryl, or optionally substituted heterocyclic; a nitrile compound; an isonitrile compound; $N_2$; $PF_3$; CS; tetrahydrothiophene; or $C_{1-5}$ alkene.

(13) The method for producing a metal complex according to Item (11) or (12), wherein the metal ion contained in the metal compound (II) is a silver ion.

(14) A hydrogenation reduction method for reducing a carbonyl compound or an imine compound by hydrogenation, the method comprising reducing a carbonyl compound or an imine compound using a hydrogen donor in the presence of the metal complex of any one of Items (1) to (10).

(15) The hydrogenation reduction method according to Item (14), wherein the carbonyl compound is at least one member selected from the group consisting of ketones, carboxylic acid esters, lactones, carboxylic acid amides, and lactams.

(16) A method for producing a carbonyl compound or an imine compound reduced by hydrogenation, the method comprising reducing a carbonyl compound or an imine compound using a hydrogen donor in the presence of the metal complex of any one of Items (1) to (10).

Advantageous Effects of Invention

The metal complex of the present invention containing a ruthenium ion or osmium ion and a tridentate aminodicarbene ligand has a very high catalytic activity even under relatively mild reaction conditions, and, for example, is capable of reducing imine compounds and carbonyl compounds, such as ketones, carboxylic acid esters, lactones, carboxylic acid amides, and lactams in the presence of a hydrogen donor to thereby produce corresponding alcohols, amines, and the like in a high yield with high catalytic efficiency.

BRIEF DESCRIPTION OF DRAWINGS

FIG. 1 schematically shows the chemical structure of complex 1 synthesized in Example 1-1.

DESCRIPTION OF EMBODIMENTS

The following describes the present invention in detail.

(1) Metal Complex

The metal complex of the present invention contains a ruthenium ion or an osmium ion and a tridentate aminodicarbene ligand.

The tridentate aminodicarbene ligand has one secondary amino group and two heterocyclic carbene groups sandwiching the amino group. The two heterocyclic carbene groups are represented by Formula $L^1$ or $L^2$:

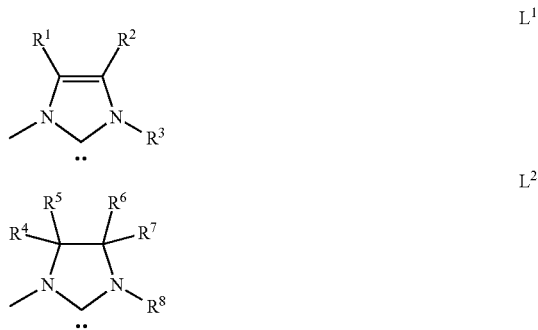

wherein $R^1$ to $R^3$ are identical or different and each represents hydrogen, halogen, hydroxyl, oxyanion (—O⁻), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^1$ and $R^2$, or $R^2$ and $R^3$, taken together, form optionally substituted divalent hydrocarbon or optionally substituted divalent heteroatom-containing hydrocarbon;

$R^4$ to $R^8$ are identical or different and each independently represents hydrogen, halogen, hydroxyl, oxyanion (—O⁻), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^5$ and $R^6$, or $R^7$ and $R^8$, taken together, form optionally substituted divalent hydrocarbon or optionally substituted divalent heteroatom-containing hydrocarbon.

The tridentate aminodicarbene ligand according to the present invention has a secondary amino group as described above, rather than a tertiary amino group or the like. In this way, the tridentate aminodicarbene ligand according to the present invention makes it possible to remarkably improve the catalytic activity. The tridentate aminodicarbene ligand further has two specific heterocyclic carbene groups sandwiching the secondary amino group, and can thus be planarly coordinated with respect to the ruthenium ion or osmium ion. This reduces the steric hindrance around the ruthenium ion or osmium ion, allowing these metal ions having catalytic activity to be well exposed, thus making it possible to remarkably improve the catalytic efficiency.

$R^1$, $R^2$, and $R^3$ of $L^1$ above represent hydrogen, halogen, hydroxyl, oxyanion (—O$^-$), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^1$ and $R^2$, and/or $R^2$ and $R^3$, taken together, form optionally substituted divalent hydrocarbon or optionally substituted divalent heteroatom-containing hydrocarbon. R', $R^2$, and re may be identical or different.

Examples of halogen represented by $R^1$, $R^2$, and $R^3$ include fluorine, chlorine, bromine, iodine, and the like.

Examples of alkyl represented by $R^1$, $R^2$, and $R^3$ include straight-chain or branched-chain alkyl having 1 to 20, and more preferably 1 to 10, carbon atoms, such as methyl, ethyl, n-propyl, isopropyl, n-butyl, sec-butyl, tert-butyl, n-pentyl, n-hexyl, n-octyl, and the like. In particular, $R^3$ is preferably straight-chain alkyl, from the viewpoint of catalyst stability, catalytic efficiency, and the like.

The alkyl may be optionally substituted. Examples of the substituents include the halogen mentioned above, oxyanion (—O$^-$), hydroxycarbonyl, nitro, cyano, sulfo, the cycloalkyl mentioned below, the aryl mentioned below, the heterocyclic mentioned below, the alkoxy mentioned below, the aryloxy mentioned below, the alkoxycarbonyl mentioned below, the carboxylic anhydride mentioned below, the acyloxy mentioned below, sulfonyloxy, silyl, optionally protected hydroxy, optionally protected amino, and the like. The number of substituents is preferably 1 to 3.

Examples of silyl as a substituent for alkyl include those in which three hydrogen atoms of silyl are replaced with the alkyl mentioned above, the aralkyl mentioned below, the aryl mentioned below, and the like. Specific examples thereof include trimethylsilyl, triethylsilyl, tert-butyldimethylsilyl, tert-butyldiphenylsilyl, triphenylsilyl, and the like.

Examples of optionally protected hydroxy as a substituent for alkyl include unprotected hydroxy; and hydroxy groups protected by a known hydroxy protecting group (e.g., trimethylsilyl, tert-butyldimethylsilyl, tert-butyldiphenylsilyl, and like silyl groups; benzyl; methoxymethyl used in peptide synthesis or the like as disclosed in Reference 1 (Protective Groups in Organic Synthesis Second Edition, JOHN WILEY & SONS, INC. 1991); and the like).

Examples of optionally protected amino as a substituent for optionally substituted alkyl include unprotected amino; amino groups protected by one or more substituents, such as N-methylamino, N,N-dimethylamino, N,N-diethylamino, N,N-diisopropylamino, N-cyclohexylamino, and like mono- or di-alkylamino groups; N-phenylamino, N,N-diphenylamino, N-naphthylamino, N-naphthyl-N-phenylamino, and like mono- or di-arylamino groups; N-benzylamino, N,N-dibenzylamino, and like mono- or di-aralkyl amino groups; formylamino, acetylamino, propionylamino, pivaloylamino, pentanoylamino, hexanoylamino, benzoylamino, and like acylamino groups; methoxycarbonylamino, ethoxycarbonylamino, n-propoxycarbonylamino, n-butoxycarbonylamino, tert-butoxycarbonylamino, pentyloxycarbonylamino, hexyloxycarbonylamino, and like alkoxycarbonylamino groups; phenyloxycarbonylamino and like aryloxycarbonylamino groups; and benzyloxycarbonylamino and like aralkyloxycarbonylamino groups. Examples of optionally protected amino include amino groups protected by a known amino protecting group used in peptide synthesis or the like as disclosed in, for example, Reference 1 above.

The alkyl above may be, for example, an aralkyl group having aryl as a substituent. Examples of aralkyl include benzyl, 1-phenyl ethyl, 2-phenyl ethyl, 1-phenylpropyl, 3-naphthylpropyl, and the like.

Examples of cycloalkyl represented by $R^1$, $R^2$, and $R^3$ include monocyclic or fused cyclic cycloalkyl having 3 to 20, and preferably 3 to 10, carbon atoms, such as cyclopropyl, cyclopentyl, cyclohexyl, and the like.

Cycloalkyl groups may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned below, the heterocyclic mentioned below, the alkoxy mentioned below, the aryloxy mentioned below, the alkoxycarbonyl mentioned below, the carboxylic anhydride mentioned below, the acyloxy mentioned below, sulfonyloxy, the silyl mentioned above, the optionally protected hydroxy mentioned above, the optionally protected amino mentioned above, and the like. The number of substituents is preferably 1 to 3.

Examples of aryl represented by $R^1$, $R^2$, and $R^3$ include monocyclic or fused cyclic aryl having 6 to 20, and preferably 6 to 14, carbon atoms, such as phenyl, naphthyl, anthryl, phenanthryl, biphenyl, and the like.

Aryl may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned below, the alkoxy mentioned below, the aryloxy mentioned below, the alkoxycarbonyl mentioned below, the carboxylic anhydride mentioned below, the acyloxy mentioned below, sulfonyloxy, the silyl mentioned above, the optionally protected hydroxy mentioned above, the optionally protected amino mentioned above, and the like. The number of substituents is preferably 1 to 3.

Examples of heterocyclic groups represented by $R^1$, $R^2$, and $R^3$ include 3- to 8-membered heterocyclic groups having 2 to 15 carbon atoms and at least one heteroatom, such as nitrogen, oxygen, and sulfur. Examples of such heterocyclic groups include aliphatic heterocyclic groups, aromatic heterocyclic groups, and the like.

Examples of aliphatic heterocyclic groups include 3- to 8-membered, preferably 4- to 6-membered, monocyclic or fused cyclic aliphatic heterocyclic groups having 2 to 14, and preferably 3 to 5, carbon atoms and at least one, preferably 1 to 3, heteroatoms, such as nitrogen, oxygen, and sulfur. Specific examples of aliphatic heterocyclic groups include azetidyl, azetidino, pyrrolidyl, pyrrolidino, piperidinyl, piperidino, piperadinyl, piperadino, morpholinyl, morpholino, tetrahydrofuryl, tetrahydropyranyl, tetrahydrothiophenyl, and the like.

Examples of aromatic heterocyclic groups include 5- or 6-membered monocyclic or fused cyclic heteroaryl groups having 2 to 15, and preferably 3 to 5, carbon atoms and at least one, preferably 1 to 3 heteroatoms, such as nitrogen, oxygen, and sulfur. Specific examples thereof include furyl, thienyl, pyridyl, pyrimidyl, pyrazyl, pyridazyl, imidazolyl, oxazolyl, thiazolyl, benzofuryl, benzothienyl, quinolyl, isoquinolyl, quinoxalyl, phthalazyl, quinazolyl, naphthyridyl, cinnolyl, benzoimidazolyl, benzoxazolyl, benzothiazolyl, acridyl, acridinyl, and the like.

Heterocyclic groups may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned below, the aryloxy mentioned below, the alkoxycarbonyl mentioned below, the carboxylic anhydride mentioned below, the acyloxy mentioned below, sulfonyloxy, the silyl mentioned above, the optionally protected hydroxy mentioned above, the optionally protected amino mentioned above, and the like. The number of substituents is preferably 1 to 3.

Examples of alkoxy represented by $R^1$, $R^2$, and $R^3$ include straight-chain or branched-chain alkoxy groups having 1 to 20, preferably 1 to 15, and more preferably 1 to 10, carbon atoms, such as methoxy, ethoxy, n-propoxy, isopropoxy, n-butoxy, isobutoxy, sec-butoxy, isobutoxy, tert-butoxy, n-pentyloxy, and the like.

Alkoxy groups may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned below, the alkoxycarbonyl mentioned below, the carboxylic anhydride mentioned below, the acyloxy mentioned below, sulfonyloxy, the silyl mentioned above, the optionally protected hydroxy mentioned above, the optionally protected amino mentioned above, and the like. The number of substituents is preferably 1 to 3. Specifically, the alkoxy may be, for example, aryl-substituted aralkyloxy. Examples of aralkyloxy include benzyloxy, 1-phenyl ethoxy, 2-phenylethoxy, 1-phenylpropoxy, 2-phenylpropoxy, 3-phenylpropoxy, 4-phenylbutoxy, 1-naphthylmethoxy, 2-naphthylmethoxy, and the like.

Examples of aryloxy represented by $R^1$, $R^2$, and $R^3$ include monocyclic or fused cyclic aryloxy groups having 6 to 18, and more preferably 6 to 14, carbon atoms. Specific examples thereof include phenoxy, tolyloxy, xylyloxy, naphthoxy, and the like.

Aryloxy groups may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned below, the carboxylic anhydride mentioned below, the acyloxy mentioned below, sulfonyloxy, the silyl mentioned above, the optionally protected hydroxy mentioned above, the optionally protected amino mentioned above, and the like. The number of substituents is preferably 1 to 3.

Examples of alkoxycarbonyl represented by $R^1$, $R^2$, and $R^3$ include straight-chain or branched-chain alkoxycarbonyl groups in which the alkoxy has 1 to 20, preferably 1 to 15, and more preferably 1 to 10, carbon atoms. Examples thereof include methoxycarbonyl, ethoxycarbonyl, n-propoxycarbonyl, isopropoxycarbonyl, n-butoxycarbonyl, isobutoxycarbonyl, sec-butoxycarbonyl, isobutoxycarbonyl, tert-butoxycarbonyl, n-pentyloxycarbonyl, and the like.

Alkoxycarbonyl groups may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the carboxylic anhydride mentioned below, the acyloxy mentioned below, sulfonyloxy, the silyl mentioned above, the optionally protected hydroxy mentioned above, the optionally protected amino mentioned above, and the like. The number of substituents is preferably 1 to 3.

Examples of carboxylic anhydride represented by $R^1$, $R^2$, and $R^3$ include straight-chain or branched-chain carboxylic anhydride groups having 1 to 20, preferably 1 to 15, and more preferably 1 to 10, carbon atoms. Examples thereof include formic anhydride, acetic anhydride, propionic anhydride, butyric anhydride, valeric anhydride, caproic anhydride, and the like.

Carboxylic anhydride groups may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the carboxylic anhydride mentioned above, the acyloxy mentioned below, sulfonyloxy, the silyl mentioned above, the optionally protected hydroxy mentioned above, the optionally protected amino mentioned above, and the like. The number of substituents is preferably 1 to 3.

Examples of amino include the optionally protected amino mentioned above. The amino may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the acyloxy mentioned below, sulfonyloxy, the silyl mentioned above, the optionally protected hydroxy mentioned above, the optionally protected amino mentioned above, and the like. The number of substituents is preferably 1 to 3.

Examples of acyloxy represented by $R^1$, $R^2$, and $R^3$ include straight-chain or branched-chain acyloxy groups having 1 to 20, preferably 1 to 15, and more preferably 1 to 10, carbon atoms. Examples of acyloxy include acetoxy, propionyloxy, butyryloxy, pivaloyloxy, trifluoroacetyloxy, benzoyloxy, pentafluorobenzoyloxy, and the like.

Acyloxy groups may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the acyloxy mentioned above, sulfonyloxy, the silyl mentioned above, the optionally protected hydroxy mentioned above, the optionally protected amino mentioned above, and the like. The number of substituents is preferably 1 to 3.

Sulfonyloxy represented by $R^1$, $R^2$, and $R^3$ may be optionally substituted. Examples of the substituents include the halogen mentioned above, oxyanion (—O$^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the acyloxy mentioned above, the silyl mentioned above, the optionally protected hydroxy mentioned above, the optionally protected amino mentioned above, and the like. The number of substituents is preferably 1 to 3.

$R^1$ and $R^2$, or $R^2$ and $R^3$, taken together, may form divalent hydrocarbon or divalent heteroatom-containing hydrocarbon. In this case, $R^1$ and $R^2$, or $R^2$ and $R^3$, taken together with the heterocyclic carbon atoms or the nitrogen to which they are attached, may form a ring. $R^1$ and $R^2$, and $R^2$ and $R^3$, taken together, may also form divalent hydrocarbon or divalent heteroatom-containing hydrocarbon. In this case, together with the heterocyclic ring, a tricyclic-fused heterocyclic carbene group is formed.

Examples of the divalent hydrocarbon formed by $R^1$ together with $R^2$, or by $R^2$ together with $R^3$ include alkylene, alkenylene, and like hydrocarbon having two or more unsaturated bonds. Examples of the divalent heteroatom-containing hydrocarbon formed by $R^1$ together with $R^2$, or by $R^2$ together with $R^3$ include oxyalkylene, and the like.

The carbon number of alkylene, alkenylene, divalent hydrocarbon having two or more unsaturated bonds, or oxyalkylene is 1 to 20, preferably 1 to 6, and more preferably 3 to 6. For example, when $R^1$ and $R^2$, taken together, form $C_4$ alkylene, $R^1$ and $R^2$, taken together with the heterocyclic carbon atoms to which $R^1$ and $R^2$ are attached, form a 6-membered ring.

When $R^1$ and $R^2$, and/or $R^2$ and $R^3$, taken together, form alkylene, the alkylene preferably has 1 to 6, and more preferably 3 to 6, carbon atoms, as stated above. Examples of preferred alkylene include propylene, butylene, pentylene, hexylene, and the like. Of these, butylene is preferable, because it is possible to form a 6-membered ring, and it is more stable.

The alkylene formed by $R^1$ together with $R^2$, and/or $R^2$ together with $R^3$ may be optionally substituted. Examples of the substituents include the halogen mentioned above, oxyanion ($-O^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the acyloxy mentioned above, sulfonyloxy, the silyl mentioned above, the optionally protected hydroxy mentioned above, the optionally protected amino mentioned above, and the like. The number of substituents is preferably 1 to 3. In this case, the substituent(s) may be attached to or fused with the ring formed by $R^1$ together with $R^2$, and/or $R^2$ together with $R^3$. For example, when $R^1$ and $R^2$, taken together with the heterocyclic carbon atoms to which $R^1$ and $R^2$ are attached, form a 6-membered ring, it is possible for cycloalkyl, arylene, and the like, to be fused with the 6-membered ring.

When $R^1$ and $R^2$, and/or $R^2$ and $R^3$, taken together, form alkenylene, the alkenylene preferably has 2 to 6, and more preferably 3 to 6, carbon atoms. Specific examples of preferred alkenylene include vinylene, 1-methylvinylene, propenylene, 1-butenylene, 2-butenylene, and the like. When $C_{3-5}$ alkenylene is formed, $R^1$ and $R^2$, and/or $R^2$ and $R^3$, taken together with the heterocyclic atoms to which each of $R^1$ and $R^2$, and/or $R^2$ and $R^3$ are attached, form a 5- to 8-membered ring having one or more unsaturated bonds in the ring.

The alkenylene formed by $R^1$ together with $R^2$, and/or $R^2$ together with $R^3$ may be optionally substituted. Examples of the substituents include the halogen mentioned above, oxyanion ($-O^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the acyloxy mentioned above, sulfonyloxy, the silyl mentioned above, the optionally protected hydroxy mentioned above, the optionally protected amino mentioned above, and the like. The number of substituents is preferably 1 to 3. In this case, the substituent(s) may be attached to or fused with the ring formed by $R^1$ together with $R^2$, and/or $R^2$ together with $R^3$. For example, when $R^1$ and $R^2$, taken together with the heterocyclic carbon atoms to which $R^1$ and $R^2$ are attached, form a 6-membered ring, it is possible for cycloalkyl, arylene, and the like, to be fused with the 6-membered ring.

When $R^1$ and $R^2$, and/or $R^2$ and $R^3$, taken together, form divalent hydrocarbon having two or more unsaturated bonds, the hydrocarbon preferably has 3 to 8, and more preferably 4 to 8, carbon atoms. Examples of the divalent hydrocarbon having two or more unsaturated bonds include $-(CH=CH)_r-$ (r is 2 or 3). Specific examples of the divalent hydrocarbon having two or more unsaturated bonds include $-CH=CH-CH=CH-$, $-CH=CH-CH=CH-CH=CH-$, 1,2-phenylene, 1,8-naphthylene, and the like.

The divalent hydrocarbon having two or more unsaturated bonds formed by $R^1$ together with $R^2$, and/or $R^2$ together with $R^3$ may be optionally substituted. Examples of the substituents include the halogen mentioned above, oxyanion ($-O^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the acyloxy mentioned above, sulfonyloxy, the silyl mentioned above, the optionally protected hydroxy mentioned above, the optionally protected amino mentioned above, and the like. The number of substituents is preferably 1 to 3. In this case, the substituent(s) may be attached to or fused with the ring formed by $R^1$ together with $R^2$, and/or $R^2$ together with $R^3$.

When $R^1$ and $R^2$, and/or $R^2$ and $R^3$, taken together, form oxyalkylene, the total of the carbon atoms and oxygen atoms of oxyalkylene is preferably 3 to 6. That is, the oxyalkylene preferably contains 1 to 5 carbon atoms and 1 to 2 oxygen atoms. Specific examples of preferred oxyalkylene include $-O-CH_2-O-$, $-CH_2-O-CH_2-$, $-O-CH_2-CH_2-$, $-O-CH_2-CH_2-O-$, $-O-CH_2-CH_2-CH_2-$. $-CH_2-O-CH_2-CH_2-$, $-O-CH_2-CH_2-CH_2-CH_2-$, $-O-CH_2-CH_2-CH_2-CH_2-CH_2-$, and the like.

The oxyalkylene formed by $R^1$ together with $R^2$, and/or $R^2$ together with $R^3$ may be optionally substituted. Examples of the substituents include the halogen mentioned above, oxyanion ($-O^-$), hydroxycarbonyl, nitro, cyano, sulfo, the alkyl mentioned above, the cycloalkyl mentioned above, the aryl mentioned above, the heterocyclic mentioned above, the alkoxy mentioned above, the aryloxy mentioned above, the alkoxycarbonyl mentioned above, the acyloxy mentioned above, sulfonyloxy, the silyl mentioned above, the optionally protected hydroxy mentioned above, the optionally protected amino mentioned above, and the like. The number of substituents is preferably 1 to 3. In this case, the substituent(s) may be attached to or fused with the ring formed by $R^1$ together with $R^2$, and/or $R^2$ together with $R^3$. For example, when $R^1$ and $R^2$, taken together with the heterocyclic carbon atoms to which $R^1$ and $R^2$ are attached, form a 6-membered ring, it is possible for cycloalkyl, arylene, and the like, to be fused with the 6-membered ring.

$R^4$, $R^5$, $R^6$, $R^7$, and $R^8$ of $L^2$ above represent hydrogen, halogen, oxyanion ($-O^-$), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy. Alternatively, $R^5$ and $R^6$, and/or $R^7$ and $R^8$, taken together, form optionally substituted divalent hydrocarbon or optionally substituted divalent heteroatom-containing hydrocarbon. $R^4$, $R^5$, $R^6$, $R^7$, and $R^8$ may be identical or different.

Halogen, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, and optionally substituted sulfonyloxy represented by $R^4$, $R^5$, $R^6$, $R^7$, and $R^8$ may be those mentioned above. Further, optionally substituted divalent hydrocarbon or optionally substituted divalent heteroatom-containing hydrocarbon formed by $R^5$ together with $R^6$, and/or $R^7$ together with $R^8$ may also be those mentioned above.

The following are preferable embodiments of $R^1$ to $R^8$ above. $R^1$ to $R^3$ are identical or different and each independently represents hydrogen, halogen, optionally substituted alkyl, optionally substituted cycloalkyl, optionally substituted aryl, optionally substituted heterocyclic, optionally substituted alkoxy, or optionally substituted aryloxy, or $R^1$ and $R^2$, and/or $R^2$ and $R^3$, taken together, form optionally substituted alkylene, optionally substituted alkenylene, or optionally substituted oxyalkylene. $R^4$ to $R^8$ are identical or different and each independently represents hydrogen, halogen, optionally substituted alkyl, optionally substituted cycloalkyl, optionally substituted aryl, optionally substituted heterocyclic, optionally substituted alkoxy, or optionally substituted aryloxy, or $R^5$ and $R^6$, and/or $R^7$ and $R^8$, taken together, form optionally substituted alkylene, optionally substituted alkenylene, or optionally substituted oxyalkylene.

Of these, from the viewpoint of yield and catalytic efficiency, $R^1$, $R^2$, $R^4$, $R^5$, $R^6$, and $R^7$ preferably represent hydrogen, the optionally substituted alkyl mentioned above, and the optionally substituted cycloalkyl mentioned above, with hydrogen being more preferable. Further, when at least one of $R^1$ and $R^2$, $R^2$ and $R^3$, $R^5$ and $R^6$, and $R^7$ and $R^8$ is substituted, it is preferable that $R^1$ and $R^2$, taken together with the adjacent carbon atoms, form a benzene ring. Specifically, $R^1$, $R^2$, $R^4$, $R^5$, $R^6$, and $R^7$ each preferably represent hydrogen, the optionally substituted alkyl mentioned above, or the optionally substituted cycloalkyl mentioned above. Alternatively, it is preferable that $R^1$ and $R^2$, taken together with the adjacent carbon atoms, form a benzene ring.

From the viewpoint of catalytic efficiency, $R^3$ and $R^8$ preferably represent optionally substituted $C_{1-20}$ alkyl, and more preferably $C_{1-6}$ alkyl. From the viewpoint of catalyst stability and catalytic efficiency, $R^3$ and $R^8$ even more preferably represent $C_{1-6}$ straight-chain alkyl.

In the present invention, the tridentate aminodicarbene ligand may contain any one or both of $L^1$ and $L^2$. From the viewpoint of catalyst stability, $L^1$ is more preferable than $L^2$.

Examples of preferred tridentate aminodicarbene ligands include a ligand represented by Formula (1):

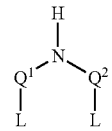

(1)

wherein $Q^1$ and $Q^2$ are identical or different and each represents optionally substituted $C_{1-5}$ alkylene or optionally substituted $C_{3-15}$ cycloalkylene, and two Ls are identical or different and each represents $L^1$ or $L^2$.

Regarding Formula (1), examples of alkylene represented by $Q^1$ and $Q^2$ include the alkylene groups mentioned above in the description of $R^1$, $R^2$, $R^3$, $R^5$, $R^6$, $R^7$, and $R^8$ of $L^1$ and $L^2$. The same applies to the substituents with which these groups may be substituted. The alkylene preferably has 1 to 3 carbon atoms. Specific examples include methylene, ethylene, propylene, and the like. $Q^1$ and $Q^2$ may be identical or different. From the viewpoint of yield and catalytic efficiency, $Q^1$ and $Q^2$ are preferably identical.

Regarding Formula (1), examples of cycloalkylene represented by $Q^1$ and $Q^2$ include a divalent group in which one hydrogen atom each is removed from two carbon atoms of monocyclic or fused cyclic cycloalkane having 3 to 15, preferably 3 to 10, and more preferably 3 to 8, carbon atoms. Examples include cyclopropylene, cyclobutylene, cyclopentylene, cyclohexylene, and the like, with cyclohexylene being preferable. Examples of substituents with which cycloalkylene may be substituted include halogen, hydroxy, oxyanion (—O$^-$), hydroxycarbonyl, nitro, cyano, sulfo, alkyl, cycloalkyl, aryl, heterocyclic, alkoxy, aryloxy, alkoxycarbonyl, carboxylic anhydride, amino, acyloxy, sulfonyloxy, silyl, optionally protected hydroxy, optionally protected amino, and the like, which are all mentioned above in the description of $R^1$, $R^2$, $R_3$, $R^4$, $R^5$, $R^6$, $R^7$, and $R^8$ of $L^1$ and $L^2$.

Of these, $Q^1$ and $Q^2$ each preferably represent methylene, ethylene, or propylene. When $Q^1$ and $Q^2$ each represent methylene, ethylene, or propylene, the tridentate aminodicarbene ligand can be more planarly coordinated with respect to a ruthenium ion or an osmium ion. This further improves the catalytic efficiency of the metal complex of the present invention. From the viewpoint of availability (e.g., ease of synthesis), catalyst stability, and catalytic efficiency, ethylene is more preferable.

The two Ls of Formula (1) represent either $L^1$ or $L^2$ above. The two Ls may be identical or different. Specifically, both of the two Ls may be $L^1$, both of the two Ls may be $L^2$, and one of the two Ls may be $L^1$ while the other one of the two Ls may be $L^2$. As described above, from the viewpoint of catalyst stability, both of the two Ls are preferably $L^1$.

The tridentate aminodicarbene ligand described above used in the present invention is not particularly limited, and is preferably a ligand represented by Formula (1A):

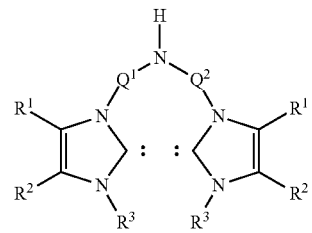

(1A)

wherein $R^1$, $R^2$, and $R^3$ are identical or different and as defined above, and $Q^1$ and $Q^2$ are identical or different and as defined above.
The tridentate aminodicarbene ligand described above used in the present invention is more preferably a ligand represented by Formula (1B) or (1C):

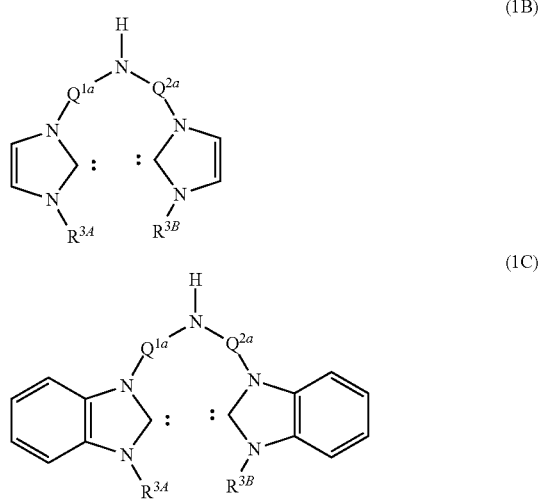

wherein $R^{3A}$ and $R^{3B}$ are identical or different and each represents $C_{1-20}$ alkyl, and $Q^{1a}$ and $Q^{2a}$ are identical or different and each represents $C_{1-5}$ alkylene or $C_{3-8}$ cycloalkylene.
$Q^{1a}$ and $Q^{2a}$ are preferably identical and preferably represent a group selected from methylene, ethylene, propylene, and cyclohexylene. Of these, ethylene is particularly preferable. $R^{3A}$ and $R^{3B}$ are preferably identical and preferably represent $C_{1-6}$ straight-chain alkyl.

The metal complex of the present invention contains a ruthenium ion or an osmium ion. The metal complex of the present invention encompasses both a mononuclear complex containing one ruthenium ion or one osmium ion, and a dinuclear complex containing a plurality of ruthenium ions and/or osmium ions. The catalytic activity is not greatly different between a mononuclear complex and a dinuclear complex (see, for example, Angew. Chem. Int. Ed. 2012, 51, 2772-2775). From the viewpoint of structural stability and the like, a mononuclear complex is preferable. From the viewpoint of catalytic activity and the like, those containing a ruthenium ion are preferable.

In addition to the tridentate aminodicarbene ligand described above, and a ruthenium ion or an osmium ion, the metal complex of the present invention may further contain, for example, a monodentate ligand that is contained in a known metal complex, as well as an anionic ligand to balance the charge.

Therefore, the metal complex of the present invention preferably has a composition represented by Formula (2) or (3):

$$[M(A)Y^1Y^2Z^1] \quad (2)$$

$$[M(A)Y^1Z^1Z^2]Y^2 \quad (3)$$

wherein M is a ruthenium ion or an osmium ion;
A represents a tridentate aminodicarbene ligand;
$Y^1$ and $Y^2$ are identical or different and each represents a monovalent anionic ligand;
$Z^1$ and $Z^2$ are identical or different and each represents a monodentate ligand.

Examples of a monovalent anionic ligand represented by $Y^1$ and $Y^2$ of Formulae (2) and (3) include hydride, alkoxy, cycloalkyloxy, aryloxy, aralkyloxy, hydroxy, acyloxy $(R^{d1}CO_2)$ sulfonyloxy $(R^{d2}SO_3)$, a halogen ion, $AlH_4^-$, $AlH_2(OCH_2CH_2OCH_3)_2^-$, $BH_4^-$, $BH_3CN^-$, $BH(C_2H_5)_3^-$, $BH(sec-C_4H_9)_3^-$, and the like.

The alkoxy, aryloxy, and aralkyloxy may be those described above.

Examples of cycloalkyloxy include monocyclic, polycyclic, or fused cyclic cycloalkyloxy having 3 to 20, preferably 3 to 10, carbon atoms, such as cyclopropyloxy, cyclopentyloxy, cyclohexyloxy, and the like.

$R^{d1}$ and $R^{d2}$ of acyloxy $(R^{d1}CO_2)$ and sulfonyloxy $(R^{d2}SO_3)$ may represent, for example, hydrogen, alkyl, cycloalkyl, aryl, or aralkyl. Examples of alkyl, cycloalkyl, aryl, and aralkyl include the alkyl, cycloalkyl, aryl, and aralkyl mentioned above in the description of $R^1$, $R^2$, $R^3$, $R^4$, $R^5$, $R^6$, $R^7$, and $R^9$ of $L^1$ and $L^2$ above. These alkyl, cycloalkyl, aryl, and aralkyl groups may further be substituted with one or more of the substituents mentioned above in the description of $R^1$, $R^2$, $R^3$, $R^4$, $R^5$, $R^6$, $R^7$, and $R^8$ of $L^1$ and $L^2$ above.

Specific preferable examples of $R^{d1}$ and $R^{d2}$ include methyl, ethyl, propyl, tert-butyl, trifluoromethyl, phenyl, pentafluorophenyl, and the like. In view of this, acyloxy is preferably acetoxy, propionyloxy, butyryloxy, pivaloyloxy, trifluoroacetyloxy, benzoyloxy, pentafluorobenzoyloxy, and the like. Further, sulfonyloxy is preferably methylsulfonyloxy, ethylsulfonyloxy, isopropylsulfonyloxy, 2,2-dimethylpropylsulfonyloxy, trifluoromethanesulfonyloxy, phenylsulfonyloxy, pentafluorophenylsulfonyloxy, and the like.

Examples of halogen ions include a fluorine ion, a chlorine ion, a bromine ion, and an iodine ion, with a chlorine ion and a bromine ion being preferable, and with a chlorine ion being even more preferable.

Of these, examples of a preferred anionic ligand include $BH_4^-$, hydride, halogen ions (in particular a chlorine ion), with halogen ions (in particular a chlorine ion) being preferable. Further, at least one of the above $Y^1$ and $Y^2$ is preferably a halogen ion.

The following describes a monodentate ligand represented by $Z^1$ and $Z^2$ of Formulae (2) and (3).

In the present invention, a two-electron donor monodentate ligand is preferably used. Examples thereof include CO, $PR^{1a}R^{1b}R^{1c}$ ($R^{1a}$, $R^{1b}$, and $R^{1c}$ are identical or different and each represents optionally substituted alkyl, optionally substituted cycloalkyl, optionally substituted aryl, or optionally substituted heterocyclic), $P(OR^{2a})(OR^{2b})(OR^{2c})$ ($R^{2a}$, $R^{2b}$, and $R^{2c}$ are identical or different and each represents optionally substituted alkyl, optionally substituted cycloalkyl, optionally substituted aryl, or optionally substituted heterocyclic), $SR^{3a}R^{3b}$ ($R^{3a}$ and $R^{3b}$ are identical or different and each represents optionally substituted alkyl, optionally substituted cycloalkyl, optionally substituted aryl, or optionally substituted heterocyclic), a nitrile compound ($R^{4a}CN$; $R^{4a}$ represents optionally substituted alkyl, optionally substituted cycloalkyl, optionally substituted aryl, or optionally substituted heterocyclic), an isonitrile compound ($R^{5a}NC$; $R^{5a}$ represents optionally substituted alkyl, optionally substituted cycloalkyl, optionally substituted aryl, or optionally substituted heterocyclic), $N_2$, $PF_3$, CS, tetrahydrothiophene, alkene having 1 to 5, preferably 2 to 5, carbon atoms, and the like.

$R^{1a}$, $R^{1b}$, $R^{1c}$, $R^{2a}$, $R^{2b}$, $R^{2c}$, $R^{3a}$, $R^{3b}$, $R^{4a}$, and $R^{5a}$ of $PR^{1a}R^{1b}R^{1c}$, $P(OR^{2a})(OR^{2b})(OR^{2c})$, $SR^{3a}R^{3b}$, a nitrile compound ($R^{4a}$CN), and an isonitrile compound ($R^{5a}$NC) may be, for example, optionally substituted alkyl, optionally substituted cycloalkyl, optionally substituted aryl, optionally substituted heterocyclic, or the like. Examples of alkyl, cycloalkyl, aryl, and heterocyclic include the alkyl, cycloalkyl, aryl, and heterocyclic mentioned above in the description of $R^1$, $R^2$, $R^3$, $R^4$, $R^5$, $R^6$, $R^7$, and $R^8$ of $L^1$ and $L^2$ above. These alkyl, cycloalkyl, aryl, and heterocyclic groups may further be substituted with one or more of the substituents mentioned above in the description of $R^1$, $R^2$, $R^3$, $R^4$, $R^5$, $R^6$, $R^7$, and $R^8$ of $L^1$ and $L^2$ above. Preferable specific examples are also as described above. Of the above, $R^{1a}$, $R^{1b}$, and $R^{1c}$ may be identical or different. $R^{2a}$, $R^{2b}$, and $R^{2c}$ may be identical or different, and $R^{3a}$ and $R^{3b}$ may be identical or different. Examples of $C_{1-5}$ alkene include ethylene, propylene, 1-butene, 2-butene, 2-methyl-2-butene, and the like.

Of these, examples of preferred monodentate ligands include CO, $PR^{1a}R^{1b}R^{1c}$ ($R^{1a}$, $R^{1b}$, and $R^{1c}$ are identical or different and each represents optionally substituted alkyl, optionally substituted cycloalkyl, optionally substituted aryl, or optionally substituted heterocyclic, all of which are described above), $P(OR^{2a})(OR^{2b})(OR^{2c})$ ($R^{2a}$, $R^{2b}$, $R^{2c}$ are identical or different and each represents optionally substituted alkyl, optionally substituted cycloalkyl, optionally substituted aryl, or optionally substituted heterocyclic), and the like.

Preferable complexes satisfying the above conditions are not particularly limited. A metal complex having the composition represented by Formula (3) is preferable, and a metal complex represented by the following Formula (3A) is more preferable.

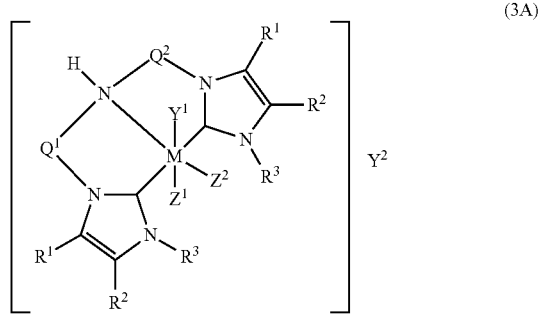
(3A)

In the formula, $R^1$, $R^2$, and $R^3$ are identical and different and as defined above;
$Q^1$ and $Q^2$ are identical and different and as defined above;
M represents a ruthenium ion or an osmium ion;
$Y^1$ and $Y^2$ are identical and different and as defined above; and
$Z^1$ and $Z^2$ are identical and different and as defined above.
Further, a metal complex represented by the following Formula (3B) or (3C) is even more preferable.

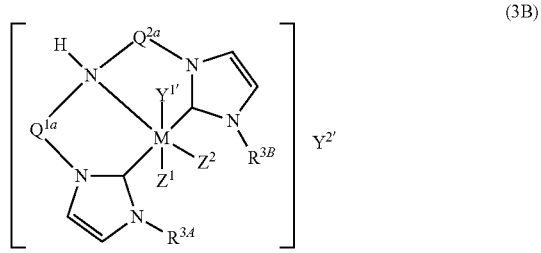
(3B)

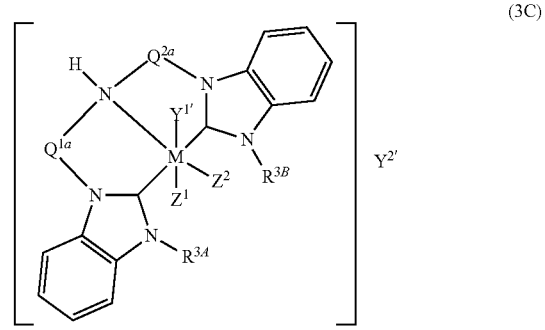
(3C)

In the formula, $R^{3A}$ and $R^{3B}$ are identical and different and as defined above;
$Q^{1a}$ and $Q^{2a}$ are identical and different and as defined above;
M is as defined above;
$Y^{1'}$ represents hydride, a halogen ion, or $BH_4^-$; and
$Y^{2'}$ represents a halogen ion.

$Q^{1a}$ and $Q^{2a}$ are preferably identical. In particular, $Q^{1a}$ and $Q^{2a}$ each preferably represent any group selected from methylene, ethylene, propylene, and cyclohexylene. $R^{3A}$ and $R^{3B}$ are preferably identical. In particular, $R^{3A}$ and $R^{3B}$ each preferably represent $C_{1-6}$ straight-chain alkyl.

Specific examples of preferred metal complexes include metal complexes represented by the following:

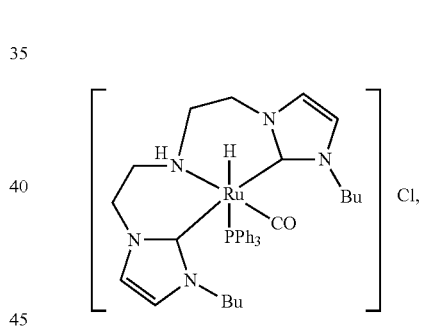

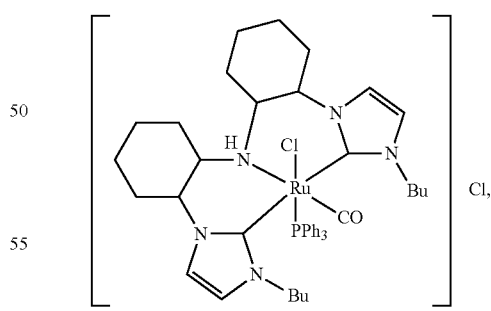

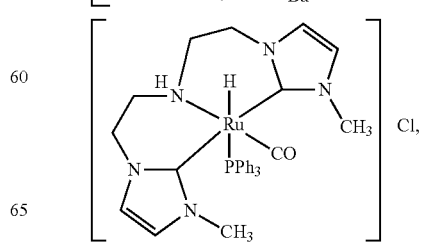

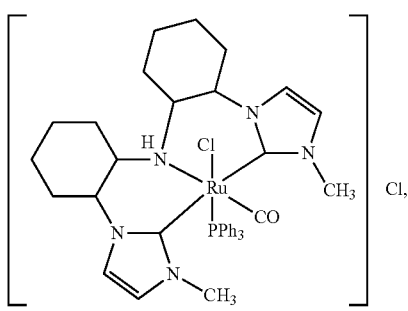

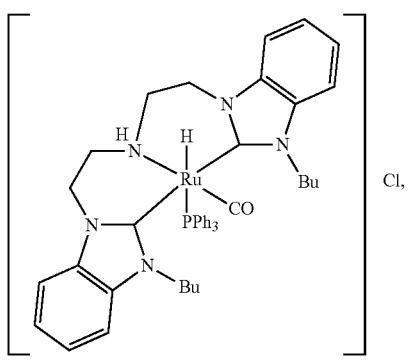

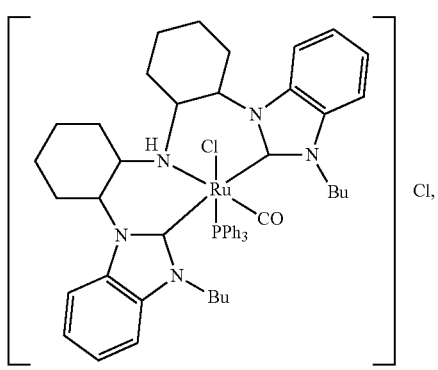

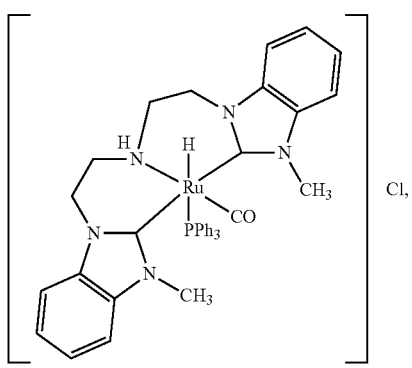

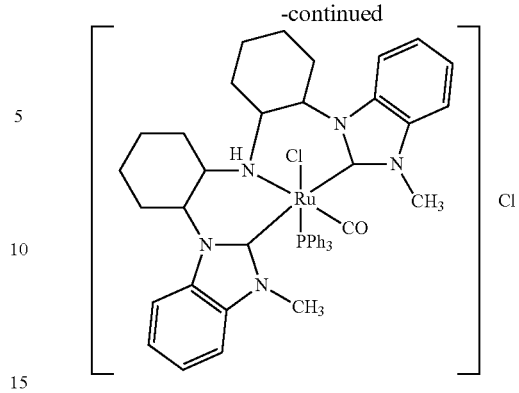

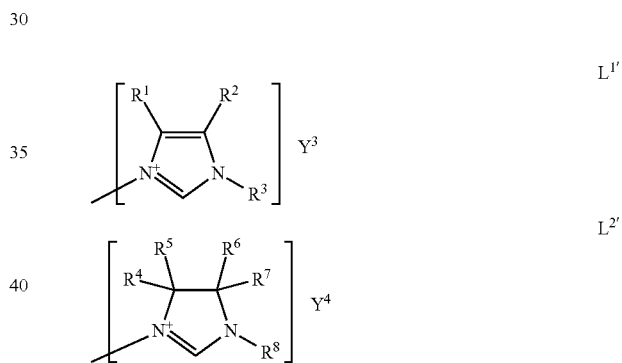

wherein Bu represents n-butyl, and Ph represents phenyl.

(2) Method for Producing a Metal Complex

The method for producing a metal complex of the present invention is not particularly limited, and method (A) may be used, comprising steps of reacting a specific metal compound (II) with a specific aminodicarbene precursor (I), and subsequently, reacting the resulting product with a specific compound (III).

The aminodicarbene precursor (I) has one secondary amino group and two heterocyclic groups sandwiching the amino group, the two heterocyclic groups being represented by Formula $L^{1'}$ or $L^{2'}$:

wherein $R^1$ to $R^3$ are identical or different and as defined above, $R^4$ to $R^8$ are identical or different and as defined above, $Y^3$ represents an anionic ligand, and $Y^4$ represents an anionic ligand.

In the production of the metal complex of the present invention, $R^1$ to $R^8$ of Formulae $L^{1'}$ and $L^{2'}$ above directly correspond to $R^1$ to $R^8$ of Formulae $L^1$ and $L^2$. Specific examples and preferable specific examples thereof are as described above.

$Y^3$ and $Y^4$ of Formulae $L^{1'}$ and $L^{2'}$ represent an anionic ligand, such as hydroxy, acyloxy ($R^{d1}CO_2^-$) ($R^{d1}$ is as defined above), sulfonyloxy ($R^{d2}SO_3^-$) ($R^{d2}$ is as defined above), a halogen ion, $BF_4^-$, $PF_6^-$, $SbF_6^-$, $BPh_4^-$, and the like. Specific or specific preferable examples of acyloxy, sulfonyloxy, and a halogen ion are as described above. Of these, a halogen ion is preferable, and a chlorine ion is more preferable.

The aminodicarbene precursor (I) preferably has $L^{1'}$ from among Formulae $L^{1'}$ and $L^{2'}$ to obtain a complex containing a ligand represented by Formula $L^1$. Such an aminodicarbene precursor (I) is preferably an aminodicarbene precursor represented by Formula (IA):

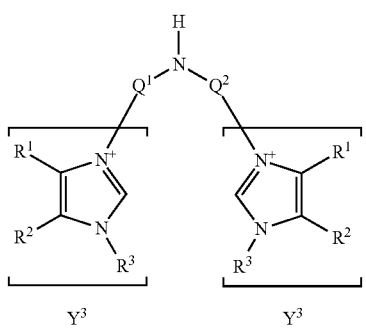

(1A)

wherein $R^1$, $R^2$, and $R^3$ are identical or different and as defined above, $Q^1$ and $Q^2$ are identical or different and as defined above, and each $Y^3$ is identical or different and as defined above. The aminodicarbene precursor (I) is more preferably an aminodicarbene precursor represented by Formula (IB) or (IC):

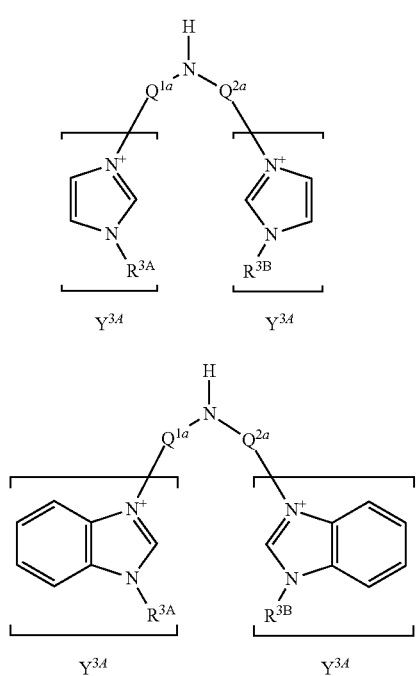

wherein $R^{3A}$ and $R^{3B}$ are identical or different and as defined above, $Q^{1a}$ and $Q^{2a}$ are identical or different and as defined above, and each $Y^{3A}$ is identical or different and represents a halogen ion. $Q^{1a}$ and $Q^{2a}$ are preferably identical. In particular, $Q^{1a}$ and $Q^{2a}$ each preferably represent any group selected from methylene, ethylene, propylene, and cyclohexylene. $R^{3A}$ and $R^{3B}$ are preferably identical. In particular, $R^{3A}$ and $R^{3B}$ each preferably represent $C_{1-6}$ straight-chain alkyl.

Examples of metal ions in the metal compound (II) include a cobalt ion, a nickel ion, a copper ion, a rhodium ion, a palladium ion, a silver ion, and the like, with a silver ion being more preferable. The metal compound (II) is preferably oxide, carbonate, sulfate, borate, phosphate, antimonate, acetate, or the like. Examples of the metal compound (II) include silver oxide, silver carbonate, silver sulfate, silver tetrafluoroborate, silver hexafluorophosphate, silver hexafluoroantimonate, silver trifluoroacetate, cobalt chloride, nickel chloride, palladium chloride, copper chloride, raney nickel, raney copper, and the like. Of these, silver oxide, silver carbonate, silver sulfate, silver tetrafluoroborate, silver hexafluorophosphate, silver hexafluoroantimonate, silver trifluoroacetate, and the like are preferable, and silver oxide is particularly preferable considering easy availability and the like.

The compound (III) is represented by Formula (4):

$$MY^1Y^2Z_n \qquad (4)$$

wherein M is a ruthenium ion or an osmium ion, $Y^1$ and $Y^2$ are identical or different and each represents a monovalent anionic ligand, Z is identical or different and each represents a monodentate ligand, and n is an integer of 2 to 4.

In Formula (4), M is a ruthenium ion or an osmium ion as described above, and is preferably a ruthenium ion as described above.

$Y^1$ and $Y^2$ each represent a monovalent anionic ligand as described above, and specific examples and specific preferable examples thereof are as described above.

Z is a monodentate ligand, and specific examples and specific preferable examples thereof are as described above for $Z^1$ and $Z^2$ of Formulae (2) and (3).

Particularly preferable examples of the compound (III) include $RuCl_2(PPh_3)_3$ (Ph is phenyl), $RuBr_2(PPh_3)_3$ (Ph is phenyl), $RuI_2(PPh_3)_3$ (Ph is phenyl), $RuHCl(PPh_3)_3$ (Ph is phenyl), $RuH(OAc)(PPh_3)_3$ (Ac is acetyl, and Ph is phenyl), $RuH_2(PPh_3)_3$ (Ph is phenyl), $RuCl_2(CH_3)_2SO$ (dimethylsulfoxide)$)_4$, $RuCl_2(CO)(PPh_3)_3$ (Ph is phenyl), $RuHCl(CO)(PPh_3)_3$ (Ph is phenyl), $RuH_2(CO)(PPh_3)_3$ (Ph is phenyl), $OsHCl(CO)(AsPh_3)_3$ (Ph is phenyl), $OsCl_2(CO)(AsPh_3)_3$ (Ph is phenyl), $OsHCl(CO)(PPh_3)_3$ (Ph is phenyl), $OsCl_2(CO)(PPh_3)_3$ (Ph is phenyl), $[OsCl_2(p\text{-cymene})]_2$, $OsCl_2(CO)(p\text{-cymene})$, $(NEt_4)_3OsCl_6$ (Et is ethyl), and the like. From the viewpoint of reaction efficiency, availability, and handling properties, $RuHCl(CO)(PPh_3)_3$ is more preferable.

The mixing ratio in the reaction of the metal compound (II) with the aminodicarbene precursor (I) is not particularly limited. From the viewpoint of yield and the like, the metal compound (II) is preferably used in an amount of 0.5 to 5 mol, and more preferably 0.9 to 1.1 mol, per mol of the aminodicarbene precursor (I). In terms of this mixing ratio, even if either the aminodicarbene precursor (I) or the metal compound (II) is excessively present, no particular problem is caused.

The reaction of the metal compound (II) with aminodicarbene precursor (I) is usually carried out in the presence of a reaction solvent. This reaction solvent may be used in an excessive amount with respect to the aminodicarbene precursor (I) and the metal compound (II). The type of solvent is not particularly limited. Examples thereof include aromatic hydrocarbons, such as toluene, xylene, and benzene; esters, such as methyl acetate, ethyl acetate, and butyl acetate; cyclic ethers, such as diethyl ether, tetrahydrofuran, dioxane, dimethoxyethane, and diisopropyl ether; halogenated hydrocarbons, such as methyl chloride, chloroform, dichloromethane, dichloroethane, and dibromoethane; ketones, such as acetone and methylethylketone; amides, such as N,N-dimethylformamide and N,N-dimethylacetamide; nitrile, such as acetonitrile; alcohols, such as methanol, ethanol, and isopropyl alcohol; dimethylsulfoxide; and the like. These may be used singly or in a combination of two or more. Of these, in the present invention, alcohols, such as methanol and ethanol are preferable.

The temperature for reacting the metal compound (II) with the aminodicarbene precursor (I) is not particularly limited. The temperature is preferably −50° C. to 30° C., and more preferably −30° C. to 0° C., and even more preferably −30 to −10° C. to further reduce the unreacted starting material remaining and to inhibit a reaction that yields a product having a structure other than the target structure.

The reaction atmosphere for reacting the metal compound (II) with the aminodicarbene precursor (I) is not particularly limited. The reaction atmosphere is preferably an inert gas atmosphere, and may be a nitrogen gas atmosphere, an argon gas atmosphere, or the like. The reaction atmosphere may also be an air atmosphere.

The reaction described above yields a dicarbene metal complex (IV) containing the tridentate aminodicarbene ligand (I) and a metal ion constituting the metal compound (II).

This dicarbene metal complex (IV) is preferably a metal complex represented by Formula (5A) or (5B):

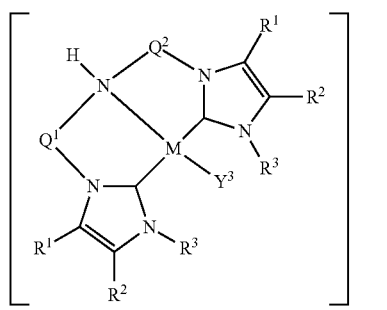

(5A)

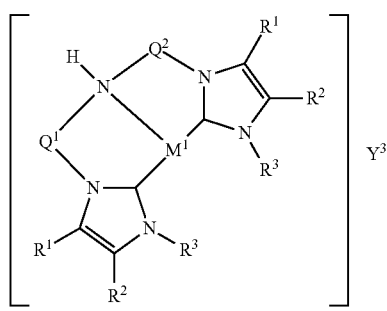

(5B)

wherein $R^1$, $R^2$, and $R^3$ are identical or different and as defined above, $Q^1$ and $Q^2$ are identical or different and as defined above, $M^1$ is a cobalt ion, a nickel ion, a copper ion, a rhodium ion, a palladium ion, or a silver ion, and $Y^3$ is as defined above. The dicarbene metal complex (IV) is more preferably a metal complex represented by Formulae (5C) to (5F):

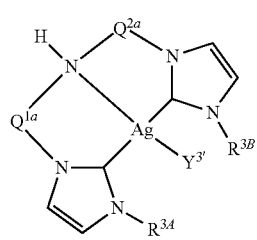

(5C)

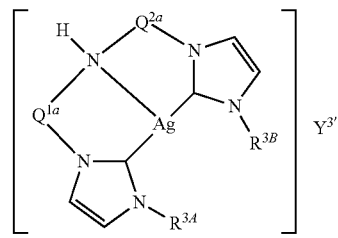

(5D)

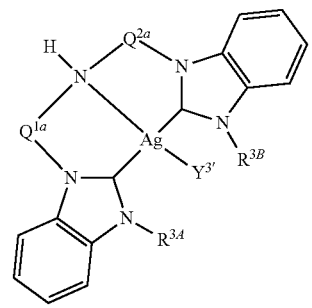

(5E)

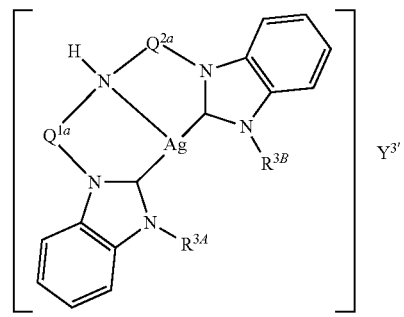

(5F)

wherein $R^{3A}$ and $R^{3B}$ are identical or different and as defined above, $Q^{1a}$ and $Q^{2a}$ are identical or different and as defined above, and $Y^{3'}$ is a halogen ion. $Q^{1a}$ and $Q^{2a}$ are preferably identical. In particular, $Q^{1a}$ and $Q^{2a}$ each preferably represent any group selected from methylene, ethylene, propylene, and cyclohexylene. $R^{3A}$ and $R^{3B}$ are preferably identical. In particular, $R^{3A}$ and $R^{3B}$ each preferably represent $C_{1-6}$ straight-chain alkyl.

The metal complex of the present invention may be prepared by isolating and purifying the dicarbene metal complex (IV) from a mixture obtained by stirring in an appropriate solvent a reaction product obtained by reacting the aminodicarbene precursor (I) and the metal compound (II), followed by reaction with the compound (III). The metal complex of the present invention may also be prepared by simplifying the steps, i.e., by directly adding the compound (III) to the mixture without isolation or purification of the dicarbene metal complex (IV) from the mixture.

Next, when the thus-obtained dicarbene metal complex (IV) is reacted with the compound (III), the mixing ratio is not particularly limited. From the viewpoint of yield and the like, the compound (III) is preferably used in an amount of 0.5 to 2 mol, and more preferably 0.9 to 1.1 mol, per mole of the dicarbene metal complex (IV).

The reaction of the dicarbene metal complex (IV) with the compound (III) is generally carried out in the presence of a reaction solvent. This reaction solvent is sufficient if used in an excessive amount with respect to the dicarbene metal complex (IV) and the compound (III), and the type of the solvent is not particularly limited. Examples thereof include aromatic hydrocarbons, such as toluene, xylene, and benzene; esters, such as methyl acetate, ethyl acetate, and butyl acetate; cyclic ethers, such as diethyl ether, tetrahydrofuran, dioxane, dimethoxyethane, and diisopropyl ether; halogenated hydrocarbons, such as methyl chloride, chloroform, dichloromethane, dichloroethane, and dibromoethane; ketones, such as acetone and methylethylketone; amides, such as dimethylformamide and dimethylacetamide; nitrile compounds, such as acetonitrile; alcohols, such as methanol, ethanol, and isopropyl alcohol; dimethylsulfoxide; and the like. These may be used singly or in a combination of two or more. Of these, in the present invention, nitrile compounds, such as acetonitrile, are preferable.

The reaction temperature for reacting the compound (III) with the dicarbene metal precursor (IV) is not particularly limited, and is usually set between 0° C. or higher and the boiling point of the reaction solvent mentioned above or lower. The reaction temperature is preferably about 20 to 70° C.

The reaction atmosphere for reacting the dicarbene metal precursor (IV) with the compound (III) is not particularly limited. The reaction atmosphere is preferably an inert gas atmosphere, and may be a nitrogen gas atmosphere, an argon gas atmosphere, or the like. The reaction atmosphere may also be an air atmosphere.

In the above manner, the metal complex of the present invention described above may be obtained.

The method for producing the metal complex of the present invention is not limited to only method (A) above. It is also possible to use method (B) comprising reacting a base (e.g., potassium tert-butoxide, lithium hexamethylenedisilazane, and sodium hydride) with the aminodicarbene precursor (I), and subsequently reacting the resulting product with the compound (III).

As other methods for producing a carbene complex, the method disclosed in Reference 2 (Wanzhi Chen et al., Organometallics 2012, 31, 282-288) may also be referred to.

Of the above, method (A) is preferable from the viewpoint of reaction efficiency, recovery, and the like.

The aminodicarbene precursor (I) may be easily obtained by reacting bis(substituted $C_{1-6}$ alkyl)amine having leaving groups, such as paratoluenesulfonyl, with at least one compound represented by Formulae $L^{1''}$ and $L^{2''}$:

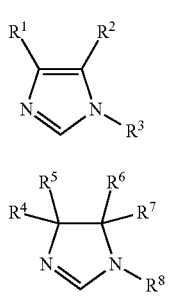

wherein $R^1$ to $R^3$ are identical or different and as defined above, and $R^4$ to $R^8$ are identical or different and as defined above. The method for obtaining the aminodicarbene precursor (I) is not limited to the above method, and the aminodicarbene precursor (I) may be synthesized by various methods with reference to known reactions.

After completion of the reaction, a usual purification method, such as extraction, filtration, reprecipitation, crystallization, distillation, and various chromatographies, may be performed singly or in a combination of two or more.

(3) Hydrogenation Reduction Method and Method for Producing a Product by Hydrogenation Reduction The following describes a hydrogenation reduction method for reducing a carbonyl compound or an imine compound by hydrogenation using a hydrogen donor in the presence of the metal complex of the present invention.

The target carbonyl compound for the hydrogenation reduction in the present invention is a divalent carbonyl-containing compound represented by C(=O)—, such as ketones, carboxylic acid esters, lactones, carboxylic acid amides, lactams, and the like. When these ketones, carboxylic acid esters, lactones, carboxylic acid amides, lactams, and the like are reduced by hydrogenation, corresponding alcohols or amines are produced.

Specific examples of ketones include formaldehyde, acetaldehyde, propionaldehyde, 1-butanal, crotonaldehyde, cyclohexanecarboxaldehyde, and like aliphatic aldehydes; benzaldehyde, 1-naphthaldehyde, 2-naphthaldehyde, and like aromatic aldehydes; acetone, 2-butanone, 2-pentanone, 3-pentanone, 3-buten-2-one, cyclopentanone, cyclohexanone, and like aliphatic ketones; acetophenone, propiophenone, benzophenone, and like aromatic ketones; and the like.

Specific examples of carboxylic acids constituting carboxylic acid esters or carboxylic acid amides include carbonic acid, formic acid, acetic acid, propionic acid, butyric acid, isobutyric acid, valeric acid, isovaleric acid, hydroangelic acid, pivalic acid, hexanoic acid, heptanoic acid, octanoic acid, nonanoic acid, decanoic acid, dodecanoic acid, lauric acid, myristic acid, palmitic acid, stearic acid, oleic acid, oxalic acid, propanedicarboxylic acid, butanedicarboxylic acid, hexanedicarboxylic acid, sebacic acid, acrylic acid, methacrylic acid, cyclopentanecarboxylic acid, cyclohexanecarboxylic acid, cyclopentenecarboxylic acid, cyclohexenecarboxylic acid, 2-azetidinecarboxylic acid, 2-pyrrolidinecarboxylic acid (proline), 3-pyrrolidinecarboxylic acid, 2-piperidinecarboxylic acid, 3-piperidinecarboxylic acid, 4-piperidinecarboxylic acid, piperazine-2-carboxylic acid, benzoic acid, naphthalenecarboxylic acid, pyridinecarboxylic acid, pyridinedicarboxylic acid, quinolinecarboxylic acid, furancarboxylic acid, thiophene carboxylic acid, and the like.

Examples of alkoxy, aralkyloxy, and aryloxy constructing carboxylic acid esters, and optionally protected amino constructing carboxylic acid amides include alkoxy, aralkyloxy, aryloxy, optionally protected amino, and the like, all of which are mentioned above in the description of $R^1$, $R^2$, $R^3$, $R^4$, $R^5$, $R^6$, $R^7$, and $R^8$ of $L^1$ and $L^2$ above.

Specific examples of lactones include β-lactone, γ-lactone, δ-lactone, and the like.

Specific examples of lactams include β-lactam, γ-lactam, δ-lactam, and the like.

Ketones, carboxylic acid esters, lactones, carboxylic acid amides, and lactams may be optionally substituted as long as the substituent does not have an adverse effect on the hydrogenation reduction method of the present invention. Examples of the substituents include the halogen, alkyl, cycloalkyl, aralkyl, aryl, heterocyclic, alkoxy, aralkyloxy, aryloxy, silyl, optionally protected hydroxy, optionally protected amino, and the like, mentioned above in the description of $R^1$, $R^2$, $R^3$, $R^4$, $R^5$, $R^6$, $R^7$, and $R^8$ of $L^1$ and $L^2$ above. In addition to the above, examples of the substituents also include alkenyl, alkynyl, cycloalkenyl, and the like.

Alkenyl may be of a straight chain or branched chain. Examples thereof include alkenyl groups having 2 to 20, preferably 2 to 15, and more preferably 2 to 10, carbon atoms. Specific examples thereof include ethenyl, propenyl, 1-butenyl, pentenyl, hexenyl, heptenyl, octenyl, nonenyl, decenyl, and the like.

Alkynyl may be of a straight chain or branched chain. Examples thereof include alkynyl groups having 2 to 20, preferably 2 to 15, and more preferably 2 to 10, carbon atoms. Specific examples thereof include ethynyl, 1-propynyl, 2-propynyl, 1-butynyl, 3-butynyl, pentynyl, hexynyl, and the like.

Examples of cycloalkenyl include 4- to 10-membered monocyclic to tricyclic aliphatic hydrocarbon groups having one or two double bonds in the ring. Specific examples thereof include cyclobutenyl, cyclopentenyl, cyclohexenyl, cycloheptenyl, cyclooctenyl, and the like.

Examples of substituents with which alkenyl, alkynyl, and cycloalkenyl may be substituted include halogen, alkyl, cycloalkyl, aralkyl, aryl, heterocyclic, alkoxy, aralkyloxy, aryloxy, silyl, and optionally protected hydroxy, all of which are mentioned above in the description of $R^1$, $R^2$, $R^3$, $R^5$, $R^6$, $R^7$, and $R^8$ of $L^1$ and $L^2$; the optionally protected amino mentioned above in the description of $R^{d1}$ and $R^{d2}$ of $Y^1$ or $Y^2$; the alkenyl, alkynyl, and cycloalkenyl mentioned above in the description of carbonyl compound; and the like.

The target carbonyl compound for the hydrogenation reduction in the present invention is an organic compound having one or more carbonyl groups. The carbonyl compound may be a monofunctional or polyfunctional compound, and may be a compound having 2 to 1,000,000 carbonyl groups in the same molecule, such as oligomer molecules or polymer molecules.

The target imine compounds for the hydrogenation reduction in the present invention are a compound obtained by dehydration condensation of the ketones mentioned above with ammonia or optionally protected primary amines. When imine compounds are reduced by hydrogenation, corresponding primary or secondary amines are produced.

Examples of optionally protected primary amines include the optionally protected amino groups mentioned above in which hydrogen is bonded to a monosubstituted amino group.

Carbonyl compounds and imine compounds are substrates that are not easily reduced by hydrogenation. However, the use of the metal complex of the present invention enables hydrogenation reduction of these substrates that are not easily reduced by hydrogenation. Of course, the use of the metal complex of the present invention enables hydrogenation reduction of other substrates that are easily reduced by hydrogenation.

Examples of hydrogen donors used in the hydrogenation reduction method of the present invention include molecular hydrogen, formic acid, primary alcohols (e.g., methanol, ethanol, 1-propanol, and 1-butanol), secondary alcohols (e.g., 2-propanol), and the like. From the viewpoint of handling properties, catalytic efficiency, and the like, molecular hydrogen is preferable.

The amount of the metal complex of the present invention used as a catalyst in the hydrogenation reduction method of the present invention varies according to the type of hydrogenated substrate, the reaction conditions, and the type of catalyst (the metal complex of the present invention). The molar ratio of the metal (a ruthenium metal or osmium metal) with respect to a hydrogenated substrate is generally within the range of 0.0001 mol % to 50 mol %, and preferably 0.0005 mol % to 5 mol %. In particular, in the present invention, even if the catalytic amount is greatly reduced, the use of the metal complex of the present invention enables hydrogenation reduction of carbonyl compounds and imine compounds, which are not easily reduced by hydrogenation.

In the hydrogenation reduction method of the present invention, an additive may optionally be suitably added in addition to the hydrogen donor and the metal complex of the present invention.

Examples of the additives include basic compounds, metal hydrides, and the like.

Examples of basic compounds include triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine, and like amines; potassium carbonate, sodium carbonate, lithium carbonate, cesium carbonate, and like alkali metal carbonates; magnesium carbonate, calcium carbonate, and like alkaline earth metal carbonates; sodium hydrogen carbonate, potassium hydrogen carbonate, and like alkali metal hydrogen carbonates; sodium hydroxide, potassium hydroxide, lithium hydroxide, and like alkali metal hydroxides; magnesium hydroxide, calcium hydroxide and like alkaline earth metal hydroxides; sodium methoxide, sodium ethoxide, sodium isopropoxide, sodium tert-butoxide, sodium 2-methyl-2-adamantoxide, potassium methoxide, potassium ethoxide, potassium isopropoxide, potassium tert-butoxide, potassium 2-methyl-2-adamantoxide, lithium methoxide, lithium ethoxide, lithium isopropoxide, lithium tert-butoxide, lithium 2-methyl-2-adamantoxide, and like alkali metal alkoxides; magnesium methoxide, magnesium ethoxide, and like alkaline earth metal alkoxides; sodium hydride, calcium hydride, and like metal hydrides; and the like. The basic compound is particularly preferably sodium methoxide or potassium tert-butoxide.

Examples of metal hydrides include lithium borohydride, sodium borohydride, potassium borohydride, lithium aluminum hydride, and the like.

The basic compounds or metal hydrides mentioned above may be used within a range that does not impair the effects of the present invention. Specifically, the basic compounds or metal hydrides may be used in an amount of 10 mol % or less (in particular 0.1 to 5 mol %) of the target carbonyl compound or imine compound to be used in the hydrogenation reduction. In this manner, it is possible to achieve a sufficiently high conversion.

The hydrogenation reduction method of the present invention may be suitably carried out in a solvent or without a solvent. It is preferable to use a solvent. It is preferable to use a solvent that can dissolve a substrate and a catalyst, and a single solvent or a mixed solvent may be used. Specific examples include toluene, xylene, and like aromatic hydrocarbons; hexane, heptane, methylcyclohexane, and like aliphatic hydrocarbons; methylene chloride, chlorobenzene, and like halogenated hydrocarbons; diethyl ether, tetrahydrofuran, methyl tert-butyl ether, cyclopentyl methyl ether, and like ethers; methanol, ethanol, n-propanol, 2-propanol, n-butanol, 2-butanol, tert-butanol, and like alcohols; ethylene glycol, propylene glycol, 1,2-propanediol, glycerin, and like polyhydric alcohols; triethylamine, N-methylmorpholine, pyridine, and like amines; and the like. Of these, aromatic hydrocarbons, ethers, and alcohols are preferable, and toluene, tetrahydrofuran, and the like are particularly preferable. The amount of the solvent used is not particularly limited. The solvent is preferably used in a proportion of 1 to 99.5 wt %, and particularly preferably 1 to 99 wt %, based on the weight of the entire reaction mixture.

In the hydrogenation reduction method of the present invention, the reaction temperature for hydrogenation reduction is not particularly limited. The temperature is preferably 0 to 200° C., and more preferably 0 to 150° C., to reduce the unreacted starting material remaining and to suppress the decomposition of, for example, the starting materials and the metal complex of the present invention. The use of the metal complex of the present invention enables, even under relatively mild conditions, hydrogenation reduction of substrates that are not easily reduced by hydrogenation. In the present invention, a solvent having a low boiling point can be used. In this case, for example, if the reaction is carried out under pressure, it is possible to allow the reaction to proceed at a temperature higher than the boiling point of the solvent.

When the hydrogenation reduction is carried out using hydrogen gas in the hydrogenation reduction method of the present invention, the pressure of hydrogen is not particularly limited. The pressure is preferably 0.1 to 10 MPa, more preferably 0.1 to 5 MPa, and even more preferably 0.1 to 1 MPa so that the unreacted starting material remaining is further reduced, the operation is not required to follow the High Pressure Gas Safety Act, and the cost for the reaction equipment can further be reduced. The use of the metal complex of the present invention enables, even under relatively mild conditions, hydrogenation reduction of a substrate that is not easily reduced by hydrogenation.

The reaction time is not particularly limited. The reaction time is 10 minutes to 100 hours, and preferably 1 to 48 hours, to achieve a sufficiently high conversion of the starting materials.

After completion of the reaction, a usual purification method, such as extraction, filtration, reprecipitation, crystallization, distillation, and various chromatographies, may be performed singly or in a combination of two or more to obtain alcohols or amines as reaction products.

EXAMPLES

The following describes the present invention in more detail. However, the present invention is not limited to the following Examples.

The conversion and selectivity were obtained by a measurement using gas chromatography (GC) under the following conditions, using the reaction mixtures obtained in each Example in which hydrogenation reaction was performed.

The following shows the conditions for analyzing the conversion and selectivity:

Analytical Method

Apparatus: GC-17A (produced by Shimadzu Glc Ltd.)

Inlet temperature: 280° C.

Detection temperature: 280° C.

Column: "DB-1MS (60 m)" (produced by J & W Scientific)

Column temperature: 40° C. (5 minutes)-15° C./minute-320° C.

Detector: a flame ionization detector (FID)

$^1$H-NMR spectra and $^{13}$C-NMR spectra were recorded on a JEOL GX-500 produced by JEOL.

The following are structures of ruthenium complexes 1 to 7 and 9 used in the following Examples and Comparative Examples.

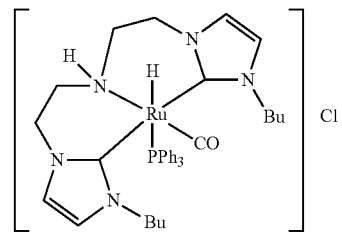

Complex 1 (Example 1-1)

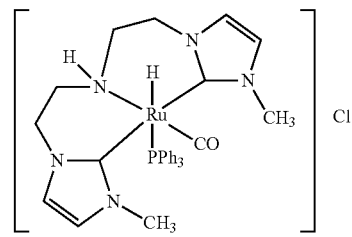

Complex 2 (Example 1-2)

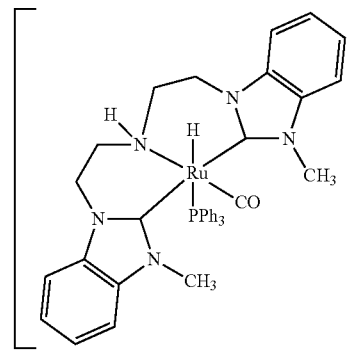

Complex 3 (Example 1-1)

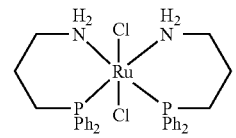

Complex 4 (Comparative Example 1-1)

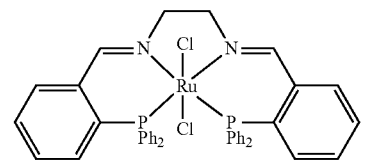

Complex 5 (Comparative Example 1-2)

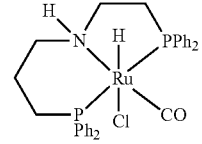

Complex 6 (Comparative Example 1-3)

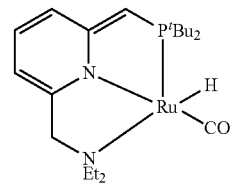

Complex 7 (Comparative Example 1-4)

-continued

Complex 9 (Comparative Example 1-6)

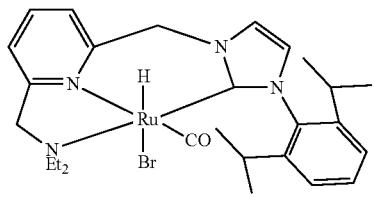

In the above formulae, Ph is phenyl, Bu is n-butyl, ᵗBu is tert-butyl, and Et is ethyl.

Example 1-1: Complex 1

Ruthenium complex 1 was produced in accordance with the following Reaction Scheme.

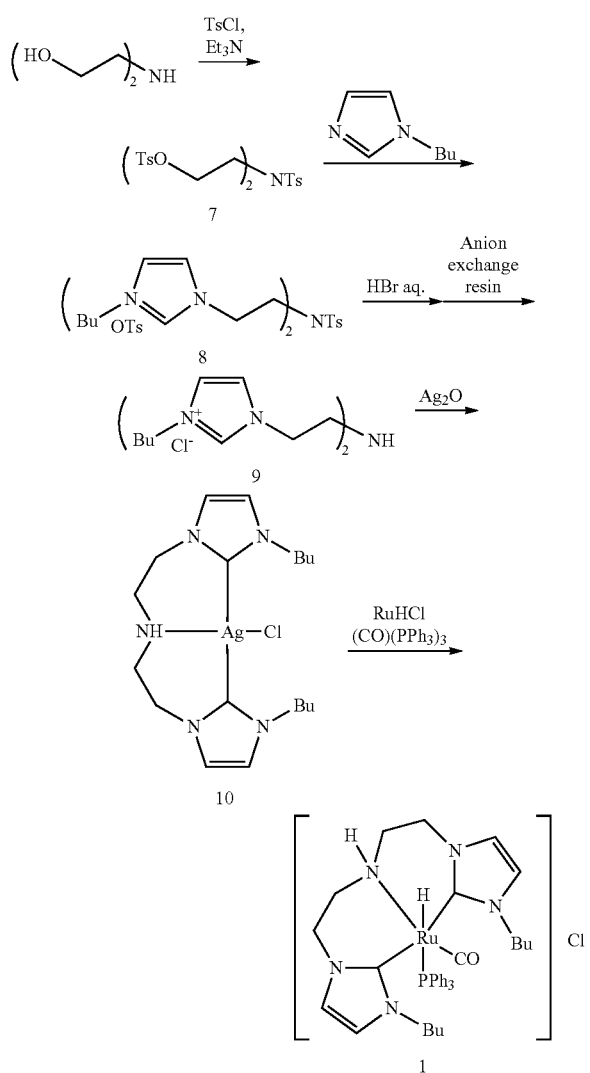

In the Reaction Scheme, Ts is paratoluenesulfonyl, Et is ethyl, Bu is n-butyl, and Ph is phenyl.

Diethanolamine to Compound 7

Under nitrogen atmosphere, 12 g (114 mmol) of diethanolamine, 62 mL (Et$_3$N, 445 mmol) of triethylamine, and toluene (160 mL) were placed in a 500-mL three-neck flask, followed by the addition of 72 g (TsCl, 378 mmol) of chloride paratoluenesulfonyl. After the addition was completed, the resulting mixture was stirred at 25° C. for 1 hour, and the solid that was formed was filtered off. Then, 100 mL of distilled water was added to the filtrate, and after separation, the organic layer was washed with a saturated saline solution (50 mL×2). The organic layer was dried over sodium sulfate and concentrated under reduced pressure to yield a crude product. This crude product was purified by silica-gel column chromatography (developer:toluene:acetone=50:1 (v/v)) to obtain 52 g (91 mmol, yield: 80%) of compound 7.

$^1$H-NMR (500 MHz, CDCl$_3$): δ=7.76 (d, J=7.9 Hz, 4H), 7.61 (d, J=7.9 Hz, 2H), 7.36 (d, J=7.9 Hz, 4H), 7.29 (d, J=7.9 Hz, 2H), 4.11 (t, J=5.8 Hz, 4H), 3.38 (t, J=5.8 Hz, 4H), 2.46 (s, 6H), 2.43 (s, 3H).

Compound 7 to Compound 8

15 g (26.4 mmol) of compound 7 produced above was placed in a 300-mL three-neck flask under nitrogen atmosphere, and 4-methyl-2-pentanone (150 mL) and 7.0 mL (53.6 mmol) of 1-butylimidazole were added thereto, followed by reflux under heating for 3 hours. After being allowed to cool down, the oily precipitate was washed with 4-methyl-2-pentanone (50 mL×2) and concentrated under reduced pressure to obtain 19.8 g (24.3 mmol, yield: 92%) of compound 8.

$^1$H-NMR (500 MHz, Deuterated DMSO): δ=9.24 (s, 2H), 7.79 (s, 2H), 7.77 (s, 2H), 7.63 (d, J=7.9 Hz, 2H), 7.49 (d, J=7.9 Hz, 4H), 7.40 (d, J=7.9 Hz, 2H), 7.12 (d, J=7.9 Hz, 4H), 4.41 (t, J=6.4 Hz, 4H), 4.15 (t, J=7.3 Hz, 4H), 3.65 (t, J=6.4 Hz, 4H), 2.41 (s, 3H), 2.29 (s, 6H), 1.75 (q, J=7.3 Hz, 4H), 1.26 (quin, J=7.3 Hz, 4H), 0.89 (d, J=7.3 Hz, 6H).

Compound 8 to Compound 9

7.2 g (8.82 mmol) of compound 8 produced above was placed in a 100-mL three-neck flask under nitrogen atmosphere, and strong hydrobromic acid (30 mL) was added thereto, followed by reflux under heating for 14 hours. After being allowed to cool down, saturated sodium hydrogen carbonate water was added thereto until the pH of the solution became 7 or more, and after the solid that was formed was filtered off, the filtrate was concentrated under reduced pressure. Then, 2-propanol (300 mL) was added to the concentrated residue, the solid that was formed was filtered off, and the filtrate was concentrated under reduced pressure. Then, water (5 mL) was added to the obtained oily compound, and the resulting solution was passed through a column with strong base type I anion exchange resin (Cl-form, Dowex™ 1×4 200-400 mesh, 30 mL) to obtain 3.4 g (8.71 mmol, yield: 99%) of compound 9.

$^1$H-NMR (500 MHz, Deuterated DMSO): δ=9.46 (s, 2H), 7.80 (s, 4H), 4.23 (t, J=5.8 Hz, 4H), 4.19 (t, J=7.3 Hz, 4H), 2.93 (m, 4H), 1.78 (q, J=7.3 Hz, 4H), 1.26 (quin, J=7.3 Hz, 4H), 0.91 (d, J=7.3 Hz, 6H).

Compound 9 to compound 10

3.4 g (8.71 mmol) of compound 9 produced above was placed in a 200-mL three-neck flask under nitrogen atmosphere, and methanol (80 mL) was added thereto, followed by cooling to −25° C. Further, 2.1 g (9.06 mmol) of silver oxide was added thereto and stirred at −25° C. for 6 hours. While the temperature was maintained at −25° C., the solution was filtered, and the solid that was formed was filtered off. Then the filtrate was concentrated under reduced pressure to obtain 3.74 g (8.12 mmol, yield: 93%) of compound 10.

$^1$H-NMR (500 MHz, Deuterated DMSO): δ=7.49 (m, 4H), 4.18 (m, 4H), 4.11 (m, 4H), 2.95 (m, 4H), 1.76 (m, 4H), 1.27 (m, 4H), 0.89 (m, 6H).

Compound 10 to compound 1

3.74 g (8.12 mmol) of compound 10 produced above was placed in a 500-mL three-neck flask under nitrogen atmosphere, and acetonitrile (190 mL) was added thereto, followed by heating to 50° C. Further, 7.48 g (8.08 mmol) of carbonylchlorohydridotris (triphenylphosphine)ruthenium (II) was added and stirred at 50° C. for 3 hours. After being allowed to cool down, the solid that was formed was filtered off, and the filtrate was concentrated under reduced pressure. Thereafter, dichloromethane (30 mL) was added to the concentrated residue, the solution was poured into hexane (300 mL), and the solid that was formed was collected by filtration. This solid was recrystallized from dichloromethane/hexane to obtain 2.3 g (3.08 mmol, yield: 38%) of the target ruthenium complex 1. Although the filtrate was concentrated in the above step, even when the filtrate was used as is without being concentrated, ruthenium complex 1 was obtained in a similar manner.

$^1$H-NMR (500 MHz, Deuterated CD$_2$Cl$_2$): δ=7.5-7.2 (m, 17H), 6.98 (s, 1H), 6.93 (s, 1H), 4.54 (t, J=5.8 Hz, 1H), 4.23 (d, J=5.8 Hz, 1H), 4.15 (d, J=5.8 Hz, 1H), 3.88 (m, 1H), 3.8-3.7 (m, 2H), 3.10 (br, 1H, N—H), 3.1-2.9 (m, 4H), 2.72 (d, J=5.8 Hz, 1H), 2.19 (m, 3H), 1.65 (m, 1H), 1.48 (m, 1H), 1.31 (m, 1H), 1.3-1.1 (m, 3H), 1.05 (m, 2H), 0.80 (t, J=5.8 Hz, 1H), −7.61 (d, $^2J_{pH}$=23.5 Hz, 1H)

$^{13}$C-NMR (150 MHz, CD$_2$Cl$_2$): δ=207 (d, Ru—$\underline{C}$O).

Complex 1 obtained in Example 1-1 was prepared as a monocrystal using dichloromethane-hexane, and X-ray structure analysis was performed using a Rigaku MerCury CCD, Crystal Clear. For the analysis, SHELXL97 of Crystal Structure 4.0 was used.

The following shows the results of the monocrystal X-ray structure analysis:
Crystal form: Triclinic
Space group: P-1
Lattice constant: a=9.338 (5), b=12.141 (6), c=19.562 (11) (unit: Å (angstrom)), β=78.89 (3), V=2087 (2) (Å$^3$ (cubic angstrom))

The following shows the bond length around the Ru:
1.658 Å (angstrom) for Ru—H;
2.265 (3) Å (angstrom) for Ru—N;
2.3702 (13) Å (angstrom) for Ru—P;
1.820 (3) Å (angstrom) for Ru—C(CO group); and
2.072 (3) Å (angstrom) and 2.128 (3) Å (angstrom), respectively, for Ru—C (carbene group).

Based on these results, FIG. 1 schematically shows the chemical structure of complex 1 synthesized in Example 1-1.

Example 1-2: Complex 2

Ruthenium complex 2 was produced in accordance with the following Reaction Scheme.

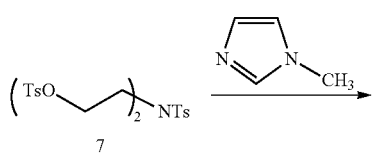

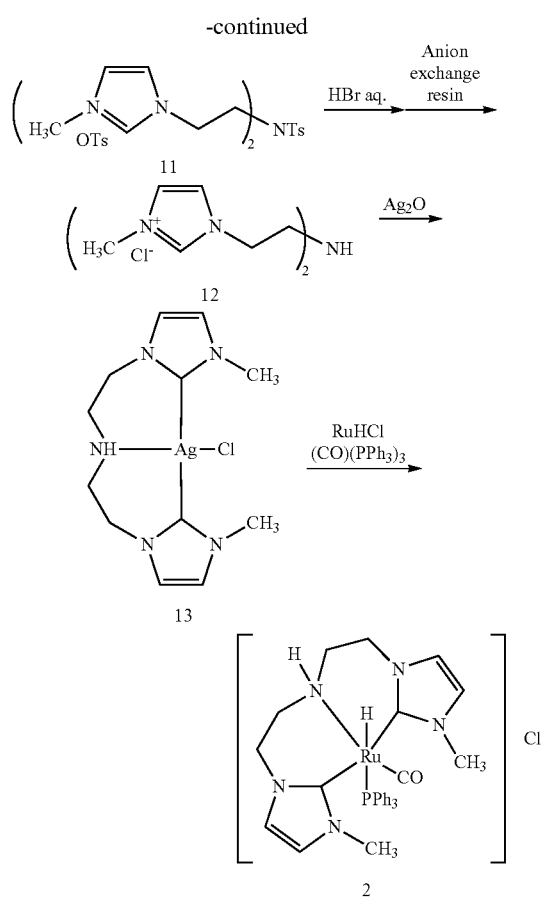

In the Reaction Scheme, Ts is paratoluenesulfonyl, and Ph is phenyl.

Compound 7 to compound 11

15 g (26.4 mmol) of compound 7 produced in Example 1-1 was placed in a 300-mL three-neck flask under nitrogen atmosphere, and 4-methyl-2-pentanone (150 mL) and 4.2 mL (53.2 mmol) of 1-methylimidazole were added, followed by reflux under heating for 3 hours. After being allowed to cool down, the oily precipitate was washed with 4-methyl-2-pentanone (50 mL×2) and concentrated under reduced pressure to obtain 18.2 g (24.9 mmol, yield: 94%) of compound 12.

$^1$H-NMR (500 MHz, Deuterated DMSO): δ=9.12 (s, 2H), 7.73 (s, 2H), 7.65 (s, 2H), 7.61 (d, J=7.9 Hz, 2H), 7.47 (d, J=7.9 Hz, 4H), 7.37 (d, J=7.9 Hz, 2H), 7.10 (d, J=7.9 Hz, 4H), 4.38 (t, J=6.2 Hz, 4H), 3.82 (s, 6H), 3.63 (t, J=7.3 Hz, 4H), 2.39 (s, 3H), 2.27 (s, 6H).

Compound 11 to Compound 12

8.0 g (10.9 mmol) of compound 11 produced above was placed in a 100-mL three-neck flask under nitrogen atmosphere, and strong hydrobromic acid (30 mL) was added thereto, followed by reflux under heating for 14 hours. After being allowed to cool down, saturated sodium hydrogen carbonate water was added thereto until the pH of the solution became 7 or more, and after the solid that was formed was filtered off, the filtrate was concentrated under reduced pressure. Then, 2-propanol (300 mL) was added to the concentrated residue, the solid that was formed was filtered off, and the filtrate was concentrated under reduced pressure. Then, water (5 mL) was added to the obtained oily compound, and the resulting solution was passed through a column with strong base type I anion exchange resin (Cl-form, Dowex™ 1×4 200-400 mesh, 30 mL) to obtain 3.2 g (10.45 mmol, yield: 96%) of compound 12.

$^1$H-NMR (500 MHz, Deuterated DMSO): δ=9.14 (s, 2H), 7.72 (s, 2H), 7.70 (s, 2H), 4.22 (t, J=5.9 Hz, 4H), 3.87 (s, 6H), 2.91 (m, 4H).

Compound 12 to Compound 13

3.2 g (10.45 mmol) of compound 12 produced above was placed in a 200-mL three-neck flask under nitrogen atmosphere, and methanol (80 mL) was added thereto, followed by cooling to −25° C. Further, 2.5 g (10.79 mmol) of silver oxide was added thereto and stirred at −25° C. for 6 hours. While the temperature was maintained at −25° C., the solution was filtered, and the solid that was formed was filtered off. Then the filtrate was concentrated under reduced pressure to obtain 3.2 g (8.49 mmol, yield: 81%) of compound 13.

$^1$H-NMR (500 MHz, Deuterated DMSO): δ=7.46 (s, 2H), 7.43 (s, 2H), 4.19 (m, 4H), 3.77 (s, 6H), 2.93 (m, 4H).

Compound 13 to Compound 2

3.06 g (8.12 mmol) of compound 13 produced above was placed in a 500-mL three-neck flask under nitrogen atmosphere, and acetonitrile (190 mL) was added thereto, followed by heating to 50° C. Further, 7.48 g (8.08 mmol) of carbonylchlorohydridotris (triphenylphosphine)ruthenium (II) was added and stirred at 50° C. for 3 hours. After being allowed to cool down, the solid that was formed was filtered off, and the filtrate was concentrated under reduced pressure. Thereafter, dichloromethane (30 mL) was added to the concentrated residue, the solution was poured into hexane (300 mL), and the solid that was formed was collected by filtration. This solid was recrystallized from dichloromethane/hexane to obtain 1.9 g (2.87 mmol, yield: 35%) of the target ruthenium complex 2. Although the filtrate was concentrated in the above step, even when the filtrate was used as is without being concentrated, ruthenium complex 2 was obtained in a similar manner.

$^1$H-NMR (500 MHz, CD$_2$Cl$_2$): δ=7.5-7.2 (m, 17H), 6.96 (s, 1H), 6.92 (s, 1H), 4.54 (t, J=5.8 Hz, 1H), 4.23 (d, J=5.8 Hz, 1H), 4.15 (d, J=5.8 Hz, 1H), 3.82 (s, 6H), 3.10 (br, 1H, N—H), 3.1-2.9 (m, 4H), 2.72 (d, J=5.8 Hz, 1H), 2.19 (m, 3H), −7.58 (d, $^2J_{PH}$=23.1 Hz, 1H)

$^{13}$C-NMR (150 MHz, Deuterated DMSO): δ=204 (d, Ru—CO).

Example 1-3: Complex 3

Ruthenium complex 3 was produced in accordance with the following Reaction Scheme.

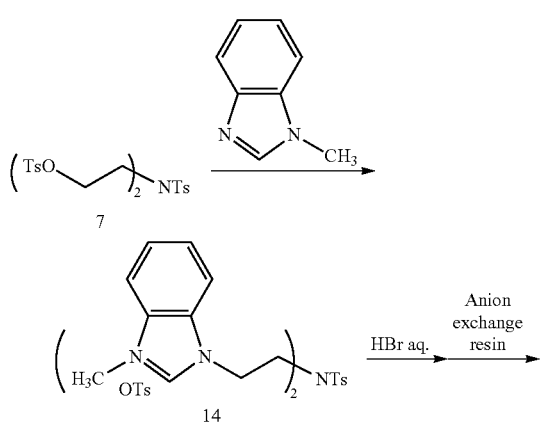

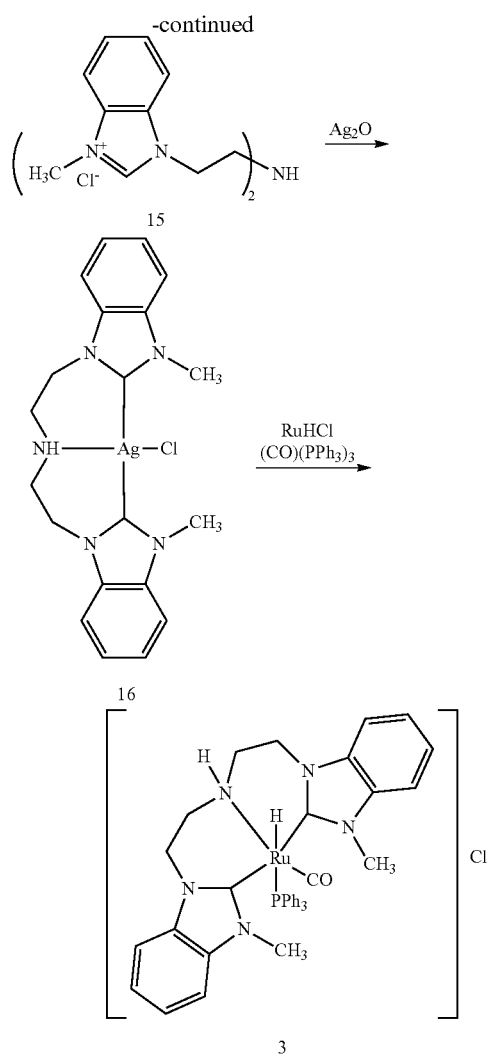

In the Reaction Scheme, Ts is paratoluenesulfonyl, and Ph is phenyl.

Compound 7 to Compound 14

15 g (26.4 mmol) of compound 7 produced in Example 1-1 was placed in a 300-mL three-neck flask under nitrogen atmosphere, and 4-methyl-2-pentanone (150 mL) and 7.1 g (53.7 mmol) of 1-methylbenzimidazole were added thereto, followed by reflux under heating for 3 hours. After being allowed to cool down, the oily precipitate was washed with 4-methyl-2-pentanone (50 mL×2) and concentrated under reduced pressure to obtain 18.1 g (21.8 mmol, yield: 82%) of compound 14.

$^1$H-NMR (500 MHz, Deuterated DMSO): δ=9.74 (s, 2H), 8.04 (m, 2H), 7.98 (m, 2H), 7.69 (m, 4H), 7.48 (d, J=8.5 Hz, 4H), 7.32 (d, J=8.5 Hz, 2H), 7.09 (d, J=8.5 Hz, 4H), 7.07 (d, J=8.5 Hz, H), 4.78 (t, J=6.0 Hz, 4H), 4.06 (s, 6H), 3.89 (t, J=6.0 Hz, 4H), 2.27 (s, 9H).

Compound 14 to Compound 15

9.1 g (10.9 mmol) of compound 14 produced above was placed in a 100-mL three-neck flask under nitrogen atmosphere, and strong hydrobromic acid (30 mL) was added thereto, followed by reflux under heating for 14 hours. After being allowed to cool down, saturated sodium hydrogen carbonate water was added thereto until the pH of the solution became 7 or more, and after the solid that was formed was filtered off, the filtrate was concentrated under reduced pressure. Then, 2-propanol (300 mL) was added to the concentrated residue, the solid that was formed was filtered off, and the filtrate was concentrated under reduced pressure. Then, water (5 mL) was added to the obtained oily compound, and the resulting solution was passed through a column with strong base type I anion exchange resin (Cl-form, Dowex™ 1×4 200-400 mesh, 30 mL) to obtain 3.6 g (8.86 mmol, yield: 81%) of compound 15.

$^1$H-NMR (500 MHz, Deuterated DMSO): δ=10.06 (s, 2H), 8.08 (d, J=7.5 Hz, 2H), 7.97 (d, J=7.5 Hz, 2H), 7.67 (t, J=7.5 Hz, 2H), 7.63 (t, J=7.5 Hz, 2H), 4.66 (m, 4H), 4.08 (s, 6H), 3.17 (m, 4H).

Compound 15 to Compound 16

3.6 g (8.86 mmol) of compound 15 produced above was added to a 200-mL three-neck flask under nitrogen atmosphere, and methanol (80 mL) was added thereto, followed by cooling to −25° C. Further, 2.1 g (9.06 mmol) of silver oxide was added thereto and stirred at −25° C. for 6 hours. While the temperature was maintained at −25° C., the solution was filtered, and the solid that was formed was filtered off. Then the filtrate was concentrated under reduced pressure to obtain 4.1 g (8.56 mmol, yield: 97%) of compound 16.

$^1$H-NMR (500 MHz, Deuterated DMSO): δ=7.82 (d, J=7.5 Hz, 2H), 7.71 (d, J=7.5 Hz, 2H), 7.41 (t, J=7.5 Hz, 2H), 7.37 (t, J=7.5 Hz, 2H), 4.63 (m, 4H), 3.98 (s, 6H), 3.19 (m, 4H).

Compound 16 to Compound 3

3.89 g (8.12 mmol) of compound 16 produced above was placed in a 500-mL three-neck flask under nitrogen atmosphere, and acetonitrile (190 mL) was added thereto, followed by heating to 50° C. Further, 7.48 g (8.08 mmol) of carbonylchlorohydridotris(triphenylphosphine)ruthenium (II) was added thereto and stirred at 50° C. for 3 hours. After being allowed to cool down, the solid that was formed was filtered off, and the filtrate was concentrated under reduced pressure. Thereafter, dichloromethane (30 mL) was added to the concentrated residue, the solution was poured into hexane (300 mL), and the solid that was formed was collected by filtration. This solid was recrystallized from dichloromethane/hexane to obtain 2.5 g (3.27 mmol, yield: 40%) of the target ruthenium complex 3. Although the filtrate was concentrated in the above step, even when the filtrate was used as is without being concentrated, ruthenium complex 3 was obtained in a similar manner.

$^1$H-NMR (500 MHz, Deuterated DMSO): δ=CD$_2$Cl$_2$): δ=7.5-7.2 (m, 19H), 6.91 (t, J=7.5 Hz, 2H), 6.88 (t, J=7.5 Hz, 2H), 4.94 (t, J=5.8 Hz, 1H), 4.56 (d, J=5.8 Hz, 1H), 4.45 (d, J=5.8 Hz, 1H), 4.05 (s, 6H), 3.31 br, 1H, N—H), 3.3-3.1 (m, 4H), 2.87 (d, J=5.8 Hz, 1H), 2.36 (m, 3H), −7.52 (d, $^2J_{PH}$=23.3 Hz, 1H)

$^{13}$C-NMR (150 MHz, Deuterated DMSO): δ=209 (d, Ru—CO).

Comparative Example 1-1: Complex 4

Dichlorobis[(2-(diphenylphosphino)ethanamine)]ruthenium purchased from Aldrich was used as is as complex 4.

Comparative Example 1-2: Complex 5

A ligand:

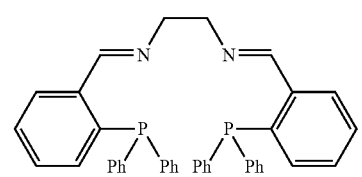

was synthesized in accordance with the disclosure of Rautenstrauch V. et al. of WO 02/40155 mentioned in PTL 2. Subsequently, complex 5 was synthesized in accordance with the section "b) using in-situ formed complex" in Example 2 of PTL 2.

Comparative Example 1-3: Complex 6

Carbonylchlorohydride[bis(2-diphenylphosphinoethyl)amino]ruthenium purchased from Strem Chemicals, Inc. was used as is as complex 6.

Comparative Example 1-4: Complex 7

Carbonylhydride[6-(di-tert-butylphosphinomethylene)-2-(N,N-diethylaminomethyl)-1,6-dihydropyridine]ruthenium purchased from Strem Chemicals, Inc. was used as is as complex 7.

Comparative Example 1-5: Complex 8

In accordance with the synthetic method used in Example 10 of PTL 5, complex 8 was synthesized by reacting an imidazolium salt (1-[(2,4,6-trimethylphenyl)methyl]-3-(3-aminopropyl)imidazolium chloride):

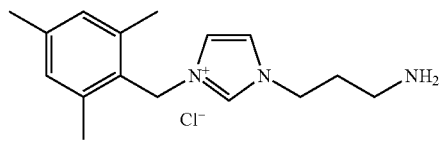 [SMILES: Cc1cc(C)c(C[n+]2ccn(CCCN)c2)c(C)c1 ; [Cl-]]

with sodium hydride and ruthenium trichloride.

Comparative Example 1-6: Complex 9

In accordance with NPL 1, compound 2a of NPL 1 was synthesized as complex 9.

Example 2-1

Methyl pivalate was hydrogenated in accordance with the following Reaction Scheme:

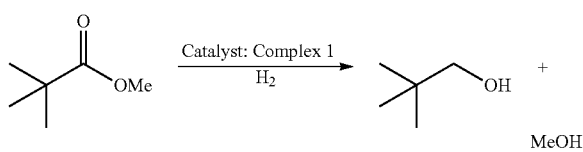

In the Reaction Scheme, Me is methyl.

Under nitrogen atmosphere, methyl pivalate (11.3 mmol), complex 1 (0.0113 mmol) produced in Example 1-1, tetrahydrofuran (60 mL), and a solution of 1M potassium tert-butoxide in tetrahydrofuran (0.57 mL) were placed in a 100-mL autoclave equipped with an electromagnetic induction stirrer, and hydrogenation reduction was performed at a hydrogen pressure of 0.65 MPa at 100° C. for 10 hours. The reaction solution was analyzed using gas chromatography. The results confirm that the conversion of methyl pivalate was 99.2%, and the selectivity to 2,2-dimethyl-1-propanol was 98%. 2,2-dimethylpropyl pivalate was obtained as a by-product.

Example 2-2

Methyl pivalate was hydrogenated as in Example 2-1, except that complex 2 (0.0113 mmol) of Example 1-2 was used in place of complex 1.

The reaction solution was analyzed using gas chromatography. The results confirm that the conversion of methyl pivalate was 99.1%, and the selectivity to 2,2-dimethyl-1-propanol was 98%. 2,2-dimethylpropyl pivalate was obtained as a by-product.

Example 2-3

Methyl pivalate was hydrogenated as in Example 2-1, except that complex 3 (0.0113 mmol) of Example 1-3 was used in place of complex 1.

The reaction solution was analyzed using gas chromatography. The results confirm that the conversion of methyl pivalate was 97.7%, and the selectivity to 2,2-dimethyl-1-propanol was 97%. 2,2-dimethylpropyl pivalate was obtained as a by-product.

Comparative Example 2-1

Methyl pivalate was hydrogenated as in Example 2-1, except that complex 4 (0.0113 mmol) of Comparative Example 1-1 was used in place of complex 1.

The reaction solution was analyzed using gas chromatography. The results confirm that the conversion of methyl pivalate was only 8.8%, and the selectivity to 2,2-dimethyl-1-propanol was 19%. 2,2-dimethylpropyl pivalate was obtained as a by-product.

Comparative Example 2-2

Methyl pivalate was hydrogenated as in Example 2-1, except that complex 5 (0.0113 mmol) of Comparative Example 1-2 was used in place of complex 1.

The reaction solution was analyzed using gas chromatography. The results confirm that the reaction did not proceed at all.

Comparative Example 2-3

Methyl pivalate was hydrogenated as in Example 2-1, except that complex 6 (0.0113 mmol) of Comparative Example 1-3 was used in place of complex 1.

The reaction solution was analyzed using gas chromatography. The results confirm that the conversion of methyl pivalate was only 8.0%, and the selectivity to 2,2-dimethyl-1-propanol was 13%. 2,2-dimethylpropyl pivalate was obtained as a by-product.

Comparative Example 2-4

Methyl pivalate was hydrogenated as in Example 2-1, except that complex 7 (0.0113 mmol) of Comparative Example 1-4 was used in place of complex 1, and that the solution of 1M potassium tert-butoxide in tetrahydrofuran (0.57 mL) was not added.

The reaction solution was analyzed using gas chromatography. The results confirm that the reaction did not proceed at all.

Comparative Example 2-5

Methyl pivalate was hydrogenated as in Example 2-1, except that complex 8 (0.0113 mmol) of Comparative Example 1-5 was used in place of complex 1.

The reaction solution was analyzed using gas chromatography. The results confirm that the conversion of methyl pivalate was only 2.0%, and the selectivity to 2,2-dimethyl-1-propanol was 8%. 2,2-dimethylpropyl pivalate was obtained as a by-product.

Comparative Example 2-6

Methyl pivalate was hydrogenated as in Example 2-1, except that complex 9 (0.0113 mmol) of Comparative Example 1-6 was used in place of complex 1.

The reaction solution was analyzed using gas chromatography. The results confirm that the conversion of methyl pivalate was only 26.0%, and the selectivity to 2,2-dimethyl-1-propanol was 74%. 2,2-dimethylpropyl pivalate was obtained as a by-product.

Example 2-4

Methyl benzoate was hydrogenated in accordance with the following Reaction Scheme:

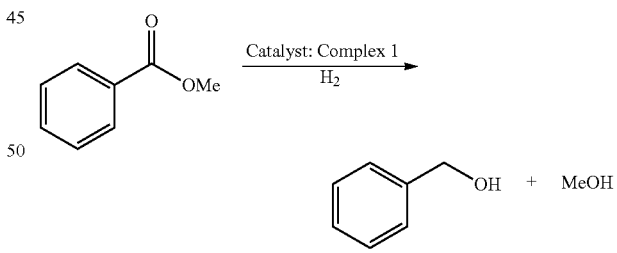

In the Reaction Scheme, Me is methyl.

Under nitrogen atmosphere, methyl benzoate (11.3 mmol), complex 1 (0.0113 mmol) produced in Example 1-1, tetrahydrofuran (60 mL), and a solution of 1M potassium tert-butoxide in tetrahydrofuran (0.57 mL) were placed in a 100-mL autoclave equipped with an electromagnetic induction stirrer, and hydrogenation reduction was performed at a hydrogen pressure of 0.65 MPa at 100° C. for 40 hours. The reaction solution was analyzed using gas chromatography. The results reveal that the conversion of methyl benzoate was 99.5%, and the selectivity to benzyl alcohol was 99.8%.

Example 2-5

In accordance with the following Reaction Scheme:

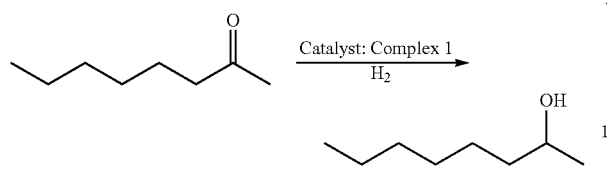

2-octanone was hydrogenated.

Under nitrogen atmosphere, 2-octanone (11.3 mmol), complex 1 (0.0113 mmol) produced in Example 1-1, tetrahydrofuran (60 mL), and a solution of 1M potassium tert-butoxide in tetrahydrofuran (0.57 mL) were placed in a 100-mL autoclave equipped with an electromagnetic induction stirrer, and hydrogenation reduction was performed at a hydrogen pressure of 0.65 MPa at 100° C. for 1 hours. The reaction solution was analyzed using gas chromatography. The results reveal that the conversion of 2-octanone was 100%, and the selectivity to 2-octanol was 100%.

Example 2-6

In accordance with the following Reaction Scheme:

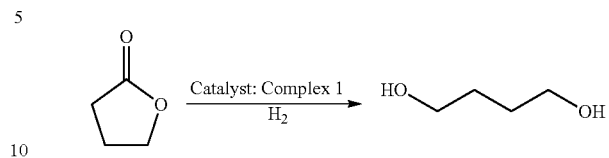

γ-butyrolactone was hydrogenated.

Under nitrogen atmosphere, γ-butyrolactone (11.3 mmol), complex 1 (0.0113 mmol) produced in Example 1-1, tetrahydrofuran (60 mL), and a solution of 1M potassium tert-butoxide in tetrahydrofuran (0.57 mL) were placed in a 100-mL autoclave equipped with an electromagnetic induction stirrer, and hydrogenation reduction was performed at a hydrogen pressure of 0.65 MPa at 100° C. for 40 hours. The reaction solution was analyzed using gas chromatography. The results reveal that the conversion of γ-butyrolactone was 100%, and the selectivity to 1,4-butanediol was 100%.

Table 1 below shows the results of Examples 2-1 to 2-6 and Comparative Examples 2-1 to 2-6.

TABLE 1

| | Complex | Carbonyl compound | Reductant | Reaction time (h) | Conversion (%) | Selectivity (%) |
|---|---|---|---|---|---|---|
| Example 2-1 | 1 | methyl pivalate | neopentyl alcohol | 10 | | |
| | | methyl pivalate | neopentyl alcohol | 10 | 99.1 | 97.7 |
| Example 2-3 | 3 | methyl pivalate | neopentyl alcohol | 10 | 97.7 | 97.1 |
| Example 2-4 | 1 | methyl benzoate | benzyl alcohol | 40 | 99.5 | 99.8 |
| Example 2-5 | 1 | 2-octanone | 2-octanol | 1 | 100 | 100 |
| Example 2-6 | 1 | γ-butyrolactone | 1,4-butanediol | 40 | 00 | 00 |
| Comp. Ex. 2-1 | | methyl pivalate | neopentyl alcohol | 10 | 8.8 | 19 |

TABLE 1-continued

| | Complex | Carbonyl compound | Reductant | Reaction time (h) | Conversion (%) | Selectivity (%) |
|---|---|---|---|---|---|---|
| Comp. Ex. 2-2 | 5 | (CH₃)₃C-C(=O)-OMe | t-BuOH | 10 | — | — |
| Comp. Ex. 2-3 | 6 | (CH₃)₃C-C(=O)-OMe | t-BuOH | 10 | 8.0 | 13 |
| Comp. Ex. 2-4 | 7 | (CH₃)₃C-C(=O)-OMe | t-BuOH | 10 | — | — |
| Comp. Ex. 2-5 | 8 | (CH₃)₃C-C(=O)-OMe | t-BuOH | 10 | 2.0 | 8.3 |
| Comp. Ex. 2-6 | 9 | (CH₃)₃C-C(=O)-OMe | t-BuOH | 10 | 26.0 | 74 |

INDUSTRIAL APPLICABILITY

The metal complex of the present invention catalyzes the hydrogenation reduction of carbonyl compounds, such as ketones, carboxylic acid esters, lactones, carboxylic acid amides, and lactams, and imine compounds that are all not easily reduced by hydrogenation under industrially advantageous conditions, i.e., at a relatively low hydrogen pressure and reaction temperature, and produces corresponding alcohols or amines in a high yield with high catalytic efficiency. Therefore, the metal complex of the present invention is useful in various industrial fields, such as food product industries, pharmaceutical industries, cosmetic industries, and fragrance industries, and in particular in the field of chemical industries, and is thus industrially applicable.

The invention claimed is:

1. A metal complex containing a ruthenium ion or an osmium ion, and a tridentate aminodicarbene ligand,
   the tridentate aminodicarbene ligand having one secondary amino group and two heterocyclic carbene groups sandwiching the amino group, the heterocyclic carbene groups being represented by Formula L¹ and/or Formula L²:

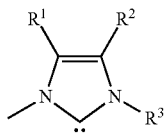

L¹

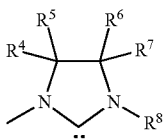

L² wherein $R^1$ to $R^3$ are identical or different and each independently represents hydrogen, halogen, hydroxyl, oxyanion (—O⁻), hydroxycarbonyl, nitro, cyano, sulfo, optionally substituted alkyl, optionally substituted cycloalkyl, optionally substituted optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or
$R^1$ and $R^2$, and/or $R^2$ and $R^3$, taken together, form optionally substituted divalent hydrocarbon or optionally substituted divalent heteroatom-containing hydrocarbon; and
$R^4$ to $R^8$ are identical or different and each independently represents hydrogen, halogen, hydroxyl, oxyanion (—O⁻), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or
$R^5$ and $R^6$, and/or $R^7$ and $R^8$, taken together, form optionally substituted divalent hydrocarbon or optionally substituted divalent heteroatom-containing hydrocarbon, wherein the tridentate aminodicarbene ligand is represented by Formula (1):

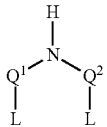
(1)

wherein $Q^1$ and $Q^2$ are identical and each represents methylene, ethylene, or propylene, and two Ls are identical or different and each represents $L^1$ or $L^2$.

2. The metal complex according to claim 1, wherein $R^1$ to $R^3$ are identical or different and each independently represents hydrogen, halogen, optionally substituted alkyl, optionally substituted cycloalkyl, optionally substituted aryl, optionally substituted heterocyclic, optionally substituted alkoxy, or optionally substituted aryloxy, or $R^1$ and $R^2$, and/or $R^2$ and $R^3$, taken together, form optionally substituted alkylene, optionally substituted alkenylene, or optionally substituted oxyalkylene; and $R^4$ to $R^8$ are identical or different and each independently represents hydrogen, halogen, optionally substituted alkyl, optionally substituted cycloalkyl, optionally substituted aryl, optionally substituted heterocyclic, optionally substituted alkoxy, or optionally substituted aryloxy, or $R^5$ and $R^6$, and/or $R^7$ and $R^8$, taken together, form optionally substituted alkylene, optionally substituted alkenylene, or optionally substituted oxyalkylene.

3. The metal complex according to any claim 1, wherein $R^3$ of Formula $L^1$ is optionally substituted alkyl, and $R^8$ of Formula $L^2$ is optionally substituted alkyl.

4. The metal complex according to claim 1, wherein $R^3$ of Formula $L^1$ is optionally substituted straight-chain alkyl, and $R^8$ of Formula $L^2$ is optionally substituted straight-chain alkyl.

5. The metal complex according to claim 1, wherein the metal complex has a composition represented by Formula (2) or (3):

(2)

(3)

wherein
M is a ruthenium ion or an osmium ion,
A is a tridentate aminodicarbene ligand,
$Y^1$ and $Y^2$ are identical or different and each represents a monovalent anionic ligand, and
$Z^1$ and $Z^2$ are identical or different and each represents a monodentate ligand.

6. The metal complex according to claim 5, wherein the monodentate ligand represents CO; $PR^{1a}R^{1b}R^{1c}$, wherein $R^{1a}$, $R^{1b}$, and $R^{1c}$ are identical or different and each represents optionally substituted alkyl, optionally substituted cycloalkyl, optionally substituted aryl, or optionally substituted heterocyclic; $P(OR^{2a})(OR^{2b})(OR^{2c})$, wherein $R^{2a}$, $R^{2b}$, and $R^{2c}$ are identical or different and each represents optionally substituted alkyl, optionally substituted cycloalkyl, optionally substituted aryl, or optionally substituted heterocyclic; $SR^{3a}R^{3b}$, wherein $R^{3a}$ and $R^{3b}$ are identical or different and each represents optionally substituted alkyl, optionally substituted cycloalkyl, optionally substituted aryl, or optionally substituted heterocyclic; a nitrile compound; an isonitrile compound; $N_2$; $PF_3$; CS; tetrahydrothiophene; or $C_{1-5}$ alkene.

7. The metal complex according to claim 5, wherein at least one of $Y^1$ and $Y^2$ of Formulae (2) and (3) is a halogen ion.

8. The metal complex according to claim 1, for use as a reduction catalyst for a reaction of reducing a carbonyl compound or an imine compound using a hydrogen donor.

9. A method for producing the metal complex according to claim 1,
the method comprising steps of reacting a metal compound (II) with an aminodicarbene precursor (I), and subsequently reacting the resulting product with a compound (III),
wherein the aminodicarbene precursor (I) has one secondary amino group and two heterocyclic groups sandwiching the amino group, the two heterocyclic groups being represented by Formula $L^{1'}$ or $L^{2'}$:

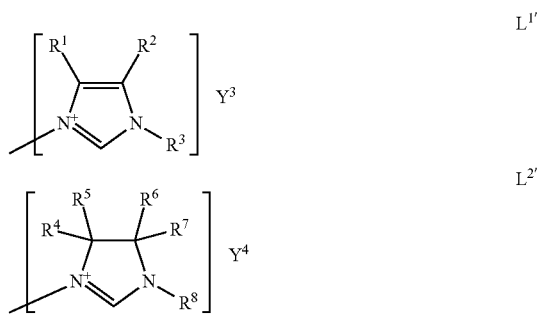

wherein $R^1$ to $R^3$ are identical or different and each independently represents hydrogen, halogen, hydroxyl, oxyanion (—O⁻), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^1$ and $R^2$, and/or $R^2$ and $R^3$, taken together, form optionally substituted divalent hydrocarbon or optionally substituted divalent heteroatom-containing hydrocarbon;

$R^4$ to $R^8$ are identical or different and each independently represents hydrogen, halogen, hydroxyl, oxyanion (—O⁻), hydroxycarbonyl, nitro, cyano, sulfo, optionally substituted alkyl, optionally substituted cycloalkyl, optionally substituted aryl, optionally substituted heterocyclic, optionally substituted alkoxy, optionally substituted aryloxy, optionally substituted alkoxycarbonyl, optionally substituted carboxylic anhydride, optionally substituted amino, optionally substituted acyloxy, or optionally substituted sulfonyloxy, or $R^5$ and $R^6$, and/or $R^7$ and $R^8$, taken together, form optionally substituted divalent hydrocarbon or optionally substituted divalent heteroatom-containing hydrocarbon;

$Y^3$ represents an anionic ligand; and
$Y^4$ represents an anionic ligand; and
wherein the metal compound (II) contains a cobalt ion, a nickel ion, a copper ion, a rhodium ion, a palladium ion, or a silver ion, and wherein the compound (III) is represented by Formula (4):

$$MY^1Y^2Z_n \quad (4)$$

wherein M represents a ruthenium ion or an osmium ion, $Y^1$ and $Y^2$ are identical or different and each represents a monovalent anionic ligand, Z is identical or different and each represents a monodentate ligand, and n is an integer of 2 to 4.

10. The method for producing a metal complex according to claim 9, wherein the monodentate ligand represents CO; $PR^{1a}R^{1b}R^{1c}$, wherein $R^{1a}$, $R^{1b}$, and $R^{1c}$ are identical or different and each represents optionally substituted alkyl, optionally substituted cycloalkyl, optionally substituted aryl, or optionally substituted heterocyclic;

$P(OR^{2a})(OR^{2b})(OR^{2c})$, wherein $R^{2a}$, $R^{2b}$, and $R^{2c}$ are identical or different and each represents optionally substituted alkyl, optionally substituted cycloalkyl, optionally substituted aryl, or optionally substituted heterocyclic; $SR^{3a}R^{3b}$, wherein $R^{3a}$ and $R^{3b}$ are identical or different and each represents optionally substituted alkyl, optionally substituted cycloalkyl, optionally substituted aryl, or optionally substituted heterocyclic; a nitrile compound; an isonitrile compound; $N_2$; $PF_3$; CS; tetrahydrothiophene; or $C_{1-5}$ alkene.

11. The method for producing a metal complex according to claim 9, wherein the metal ion contained in the metal compound (II) is a silver ion.

12. A hydrogenation reduction method for reducing a carbonyl compound or an imine compound by hydrogenation, the method comprising reducing a carbonyl compound or an imine compound using a hydrogen donor in the presence of the metal complex of claim 1.

13. The hydrogenation reduction method according to claim 12, wherein the carbonyl compound is at least one member selected from the group consisting of ketones, carboxylic acid esters, lactones, carboxylic acid amides, and lactams.

14. A method for producing a carbonyl compound or an imine compound reduced by hydrogenation, the method comprising reducing a carbonyl compound or an imine compound using a hydrogen donor in the presence of the metal complex of claim 1.

* * * * *